(12) United States Patent
Fujisaki et al.

(10) Patent No.: US 9,055,939 B2
(45) Date of Patent: Jun. 16, 2015

(54) TISSUE LIGATING DEVICE

(75) Inventors: Ken Fujisaki, Sagamihara (JP); Takumi Isoda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 33 days.

(21) Appl. No.: 13/306,102

(22) Filed: Nov. 29, 2011

(65) Prior Publication Data
US 2012/0165865 A1  Jun. 28, 2012

(30) Foreign Application Priority Data

Nov. 30, 2010  (JP) ................................. 2010-267776
Nov. 28, 2011  (JP) ................................. 2011-258684

(51) Int. Cl.
*A61B 17/04* (2006.01)
*A61B 17/12* (2006.01)

(52) U.S. Cl.
CPC ............. *A61B 17/0487* (2013.01); *A61B 17/12* (2013.01)

(58) Field of Classification Search
CPC ............. A61B 17/122; A61B 17/0485; A61B 17/0487; A61B 17/12
USPC ......... 606/110–113, 127–128, 139, 143–144, 606/148–151, 157–158, 203, 228–233; 24/115 A, 129 W, 129 R
See application file for complete search history.

(56) References Cited

U.S. PATENT DOCUMENTS

| | | | | |
|---|---|---|---|---|
| 340,239 A * | 4/1886 | Palmer | | 24/129 R |
| 773,317 A * | 10/1904 | Funke | | 5/122 |
| 1,047,654 A * | 12/1912 | Klersy | | 43/44.85 |
| 2,884,478 A * | 4/1959 | Becker et al. | | 174/94 R |
| 3,002,780 A * | 10/1961 | Eggeman | | 294/74 |
| 3,353,232 A * | 11/1967 | Brownson | | 24/129 R |
| 5,372,604 A * | 12/1994 | Trott | | 606/232 |
| 5,665,109 A | 9/1997 | Yoon | | |
| 5,879,371 A | 3/1999 | Gardiner et al. | | |
| 6,533,802 B2 | 3/2003 | Bojarski et al. | | |
| 7,530,990 B2 | 5/2009 | Perriello et al. | | |
| 7,862,584 B2 * | 1/2011 | Lyons et al. | | 606/232 |
| 8,187,301 B2 * | 5/2012 | Lyons et al. | | 606/232 |
| 8,267,962 B2 * | 9/2012 | Stupak | | 606/232 |
| 8,454,635 B2 * | 6/2013 | Paolitto et al. | | 606/158 |
| 2002/0065536 A1 * | 5/2002 | Hart et al. | | 606/232 |

(Continued)

FOREIGN PATENT DOCUMENTS

| | | |
|---|---|---|
| EP | 0 594 002 A1 | 4/1994 |
| EP | 0 594 002 | 5/1997 |

(Continued)

OTHER PUBLICATIONS www.merriam-webster.com/dictionary/suture, definition of the term suture retrieved on Mar. 31, 2014.*

(Continued)

*Primary Examiner* — David Eastwood
(74) *Attorney, Agent, or Firm* — Scully, Scott, Murphy & Presser, PC

(57) ABSTRACT

A tissue ligating device to which a suture is attached and which ligates a tissue includes a suture fix member which is attached to the suture, and which includes a housing part which one part of the suture can be hooked; and a hooked suture locking part configured to prevent the suture hooked in the housing part from disengaging from the housing part.

18 Claims, 18 Drawing Sheets

(56) References Cited

U.S. PATENT DOCUMENTS

| | | | |
|---|---|---|---|
| 2003/0093091 A1* | 5/2003 | Paolitto et al. | 606/139 |
| 2004/0015171 A1 | 1/2004 | Bojarski et al. | |
| 2004/0260344 A1* | 12/2004 | Lyons et al. | 606/232 |
| 2005/0038459 A1* | 2/2005 | Hart et al. | 606/157 |
| 2006/0135969 A1* | 6/2006 | Assia | 606/151 |
| 2006/0179618 A1* | 8/2006 | Radford | 24/129 R |
| 2008/0103513 A1* | 5/2008 | Assia | 606/151 |
| 2008/0287991 A1 | 11/2008 | Fromm | |
| 2009/0118746 A1* | 5/2009 | Assia | 606/151 |
| 2010/0031479 A1* | 2/2010 | Apicella | 24/129 R |
| 2010/0160957 A1* | 6/2010 | Kirkham | 606/203 |
| 2012/0136389 A1* | 5/2012 | Ashley et al. | 606/232 |
| 2013/0133240 A1* | 5/2013 | Beitzel | 43/43.16 |

FOREIGN PATENT DOCUMENTS

| | | |
|---|---|---|
| JP | 10-337291 | 12/1998 |
| JP | 2001-508316 A | 6/2001 |
| JP | 2002-515281 A | 5/2002 |
| JP | 3587571 | 8/2004 |
| JP | 2004-528121 | 9/2004 |
| WO | WO 97/25927 A1 | 7/1997 |
| WO | WO 99/59476 A1 | 11/1999 |
| WO | WO 02/091959 A1 | 11/2002 |

OTHER PUBLICATIONS www.thefreedictionary.com/suture, definition of the term suture retrieved Mar. 31, 2014.*

International Search Report PCT/JP2011/077498 dated Dec. 27, 2011 together with an English language translation.

English-language Abstract of Japanese Patent Publication No. 08-140982, dated Jun. 4, 1996.

* cited by examiner

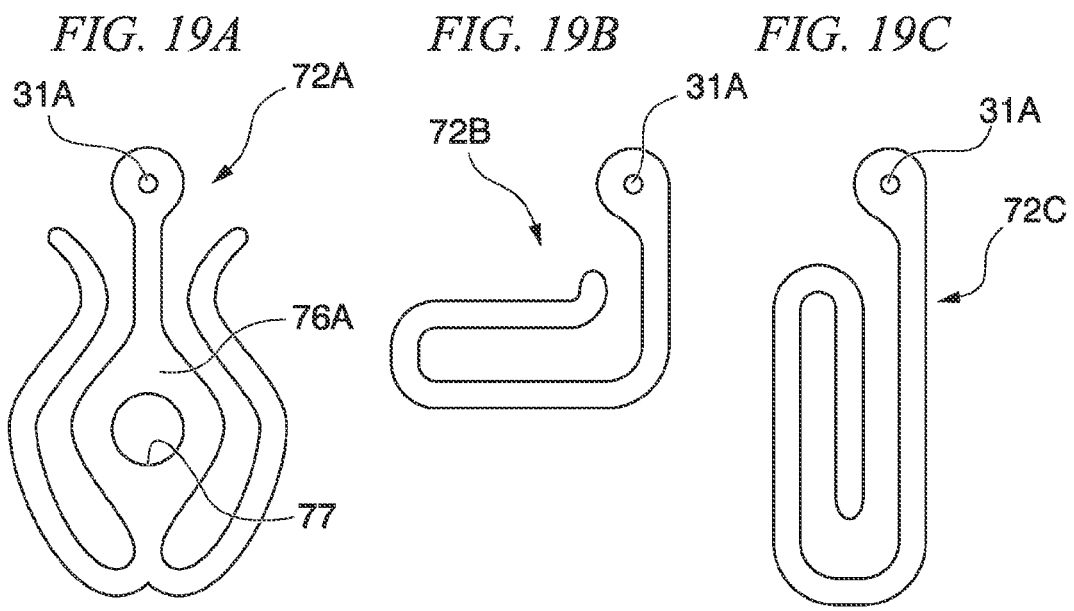
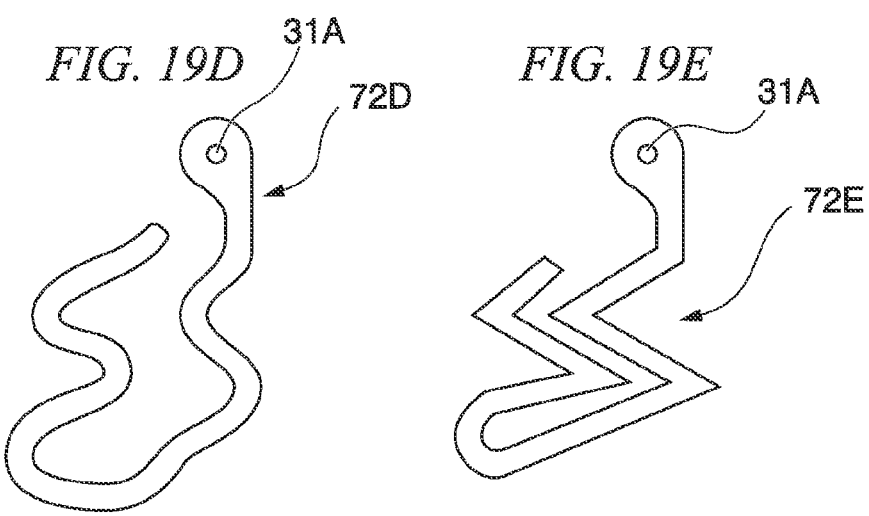
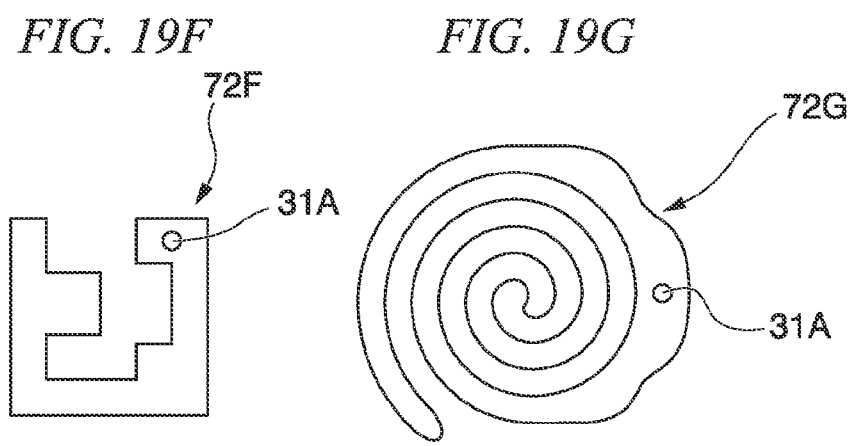

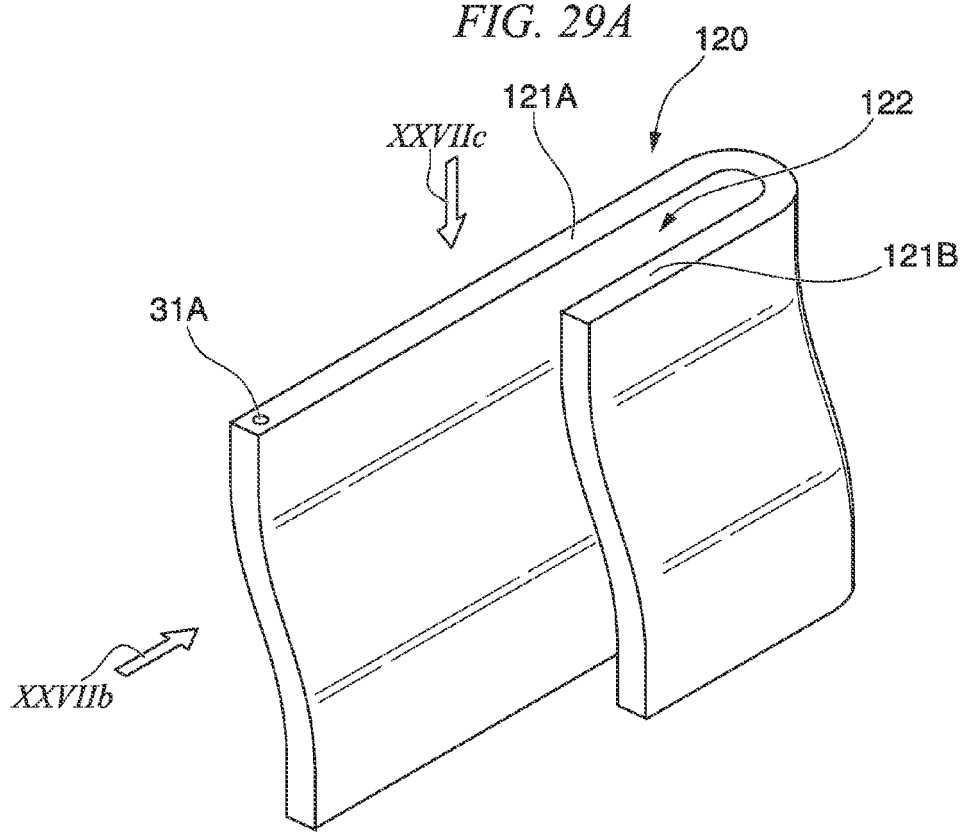
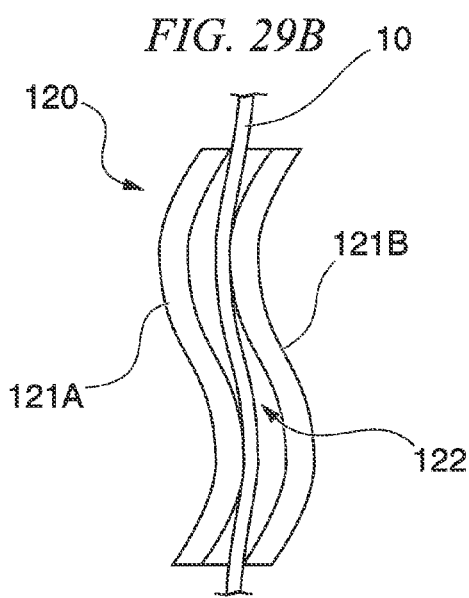
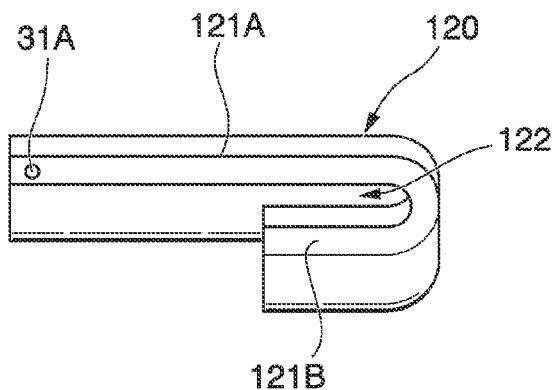

TISSUE LIGATING DEVICE

BACKGROUND OF THE INVENTION

1. Field of Invention

The present invention relates to a tissue ligating device, and more specifically relates to a tissue ligating device including a suture and a suture fix member. Priority is claimed on Japanese Patent Application No. 2010-267776, filed Nov. 30, 2010, and Japanese Patent Application No. 2011-258684, filed Nov. 28, 2011, the contents of which are incorporated herein by reference.

2. Description of Related Art

The suturing and ligating tissue are very important operations in the field of medical treatment. These operations are also extremely difficult and require considerable skill. Recently, for the purpose of reducing the invasiveness for the patient, various types of procedures in surgery or the like using an endoscope, a laparoscope, a thoracoscope or the like, have been attempted. A suture instrument for medical treatment proposed in Japanese Published Unexamined Application No. H 8-140982 includes a suture unit where a suture is connected to a suture fix member. The suture fix member has a housing part capable of housing one part of the suture. After the suture which is threaded into tissue using a curved needle or the like, is inserted into the housing part and is drawn tight, the housing part is deformed by swage or ultrasonic waves or the like, whereby one part of the suture trapped in the housing part is fixed to the suture fix member. As a result, since a knot is formed, the knot can be formed easily.

SUMMARY OF THE INVENTION

A tissue ligating device according to a first aspect of the invention is a tissue ligating device to which a suture is attached and which ligates a tissue, and includes a suture fix member which is attached to the suture, and which includes a housing part where one part of the suture can be hooked, and a hooked suture locking part configured to prevent the suture hooked in the housing part from disengaging from the housing part.

In a tissue ligating device according a second aspect of the invention, the hooked suture locking part is formed on the suture fix member.

The hooked suture locking part may include a protrusion protruding into the housing part. The hooked suture locking part may include a constriction part causes the size of the housing part to become smaller than at other points viewed from at least one direction.

Moreover, the configuration may be one where the housing part bends viewed from at least one direction, and in this bent state the housing part functions as the hooked suture locking part.

The tissue ligating device according a third aspect of the invention further includes a suture attached to the suture fix member.

The tissue ligating device according to a fourth aspect of the invention further includes a suture needle attached to one end of the suture.

BRIEF DESCRIPTION OF THE DRAWINGS

FIG. 19A is a front view of a suture fix member in a modified example of the tissue ligating device according to the third embodiment of the invention.

FIG. 19B is a front view of a suture fix member in a modified example of the tissue ligating device according to the third embodiment of the invention.

FIG. 19C is a front view of a suture fix member in a modified example of the tissue ligating device according to the third embodiment of the invention.

FIG. 19D is a front view of a suture fix member in a modified example of the tissue ligating device according to the third embodiment of the invention.

FIG. 19E is a front view of a suture fix member in a modified example of the tissue ligating device according to the third embodiment of the invention.

FIG. 19F is a front view of a suture fix member in a modified example of the tissue ligating device according to the third embodiment of the invention.

FIG. 19G is a front view of a suture fix member in a modified example of the tissue ligating device according to the third embodiment of the invention.

FIG. 29A is a view of a suture fix member in a tissue ligating device in a modified example of the invention.

FIG. 29B is a view of a suture fix member in a tissue ligating device in a modified example of the invention.

FIG. 29C is a view of a suture fix member in a tissue ligating device in a modified example of the invention.

DETAILED DESCRIPTION OF THE INVENTION

A first embodiment of the invention will be explained with reference to FIGS. 1 to 12B.

Figure 1:
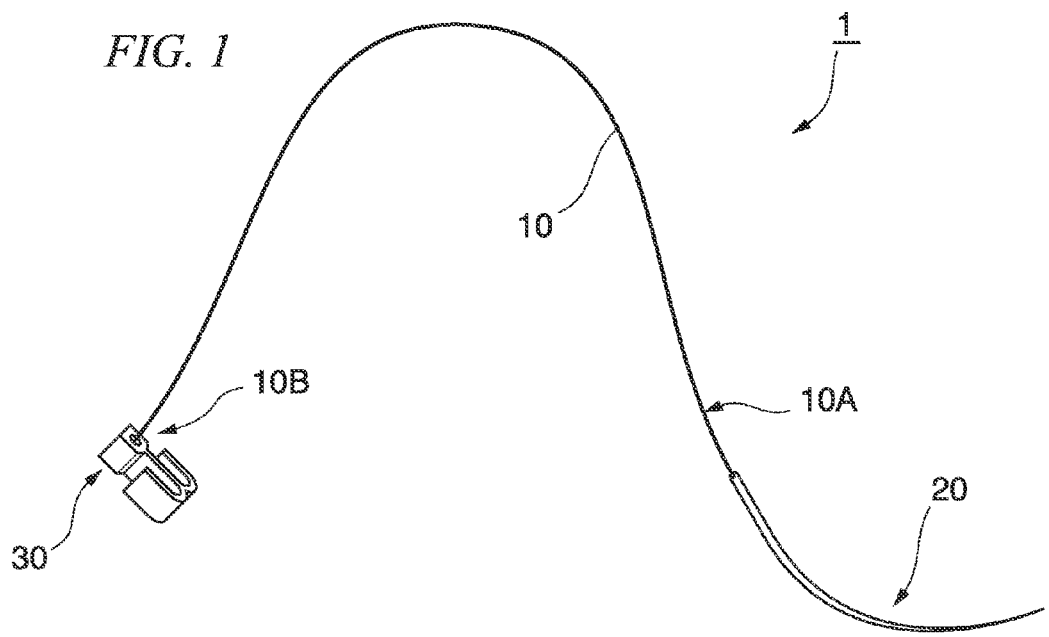
FIG. 1 is a view of a tissue ligating device according to a first embodiment of the invention.

FIG. 1 is a view of a tissue ligating device (hereinafter referred as 'ligating device') 1 of this embodiment. The ligating device 1 includes a suture 10, a suture needle 20 attached to a first end 10A of the suture 10, and a suture fix member 30 attached to a second end 10B of the suture 10.

The suture 10 is preferably a member made of resin or metal that maintains a linear shape and has a certain degree of elasticity; however, a member without elasticity can also be used. For example, when the suture 10 is made of resin, it is preferably made of a bioabsorbable resin, since this has advantages such as eliminating the need for suture removal (in this case, the suture fix member is preferably also made of absorbable resin). However, the suture 10 can be made of a non-absorbable resin. As the suture 10, a monofilament member (single wire) or a multifilament member (plural wires) can be used depending on the intended purpose. A member with a multiple-layer structure can be used as the monofilament member, such as a single wire made from a single material, or a member with a two-layer structure including a core made from a material with high tensile strength and a cladding made from a material with good welding properties. As the multifilament member, either of a member made by weaving a plurality of wires and a member made by twisting can be used. The multifilament member can also be formed by combining wires made from a plurality of different materials.

Various types of well-known suture needles can be used as the suture needle 20. After considering the suture position, the suture needle 20 can be selected as appropriate from among a linear suture needle, a curved suture needle, a suture needle that has a curved tip and is otherwise straight, and so on. There are no particular restrictions on the manner of connecting the suture 10 and the suture needle 20. The only requirement is that the suture 10 and the suture needle 20 can maintain their state of connection with respect to the amount of force acting on the point where they are connected during a knot-formation operation and an operation of passing the suture through tissue described below. Specific methods for tying the suture 10 to the suture needle 20 that can be used include adhesion, welding, or passing one end of the suture 10 through a hole formed in one end of the suture needle 20.

Figure 2:
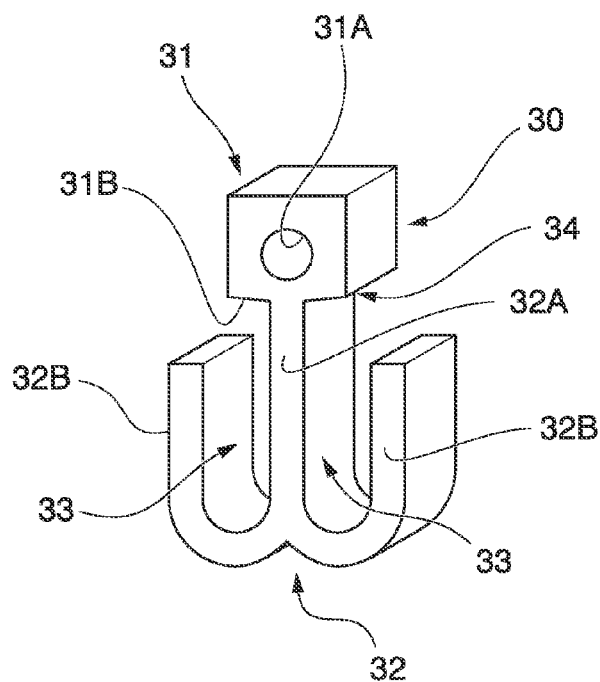
FIG. 2 is an enlarged perspective view of a suture fix member of the tissue ligating device according to the first embodiment of the invention.

FIG. 2 is an enlarged perspective view of the suture fix member 30. The suture fix member 30 is made from metal, resin, or the like. The suture fix member 30 includes a connection part 31 which the second end 10B of the suture 10 is connected to, and an arm part 32 that extends from the connection part 31.

The connection part 31 is substantially a rectangular parallelepiped, and has an insertion hole 31A which the second end 10B of the suture 10 is inserted into. The second end 10B is inserted into the insertion hole 31A. The suture 10 and the suture fix member 30 are then connected and attached to the second end 10B using an adhesive or the like.

The arm part 32 includes a first arm part 32A that extends from the connection part 31, and second arm parts 32B that branch from the first arm part 32A and extend after being folded to the connection part side. The first arm part 32A extends from one side part 31B in a front view of the suture fix member 30 (when the suture fix member 30 is viewed from the face where the insertion hole 31A opens), and extends linearly in a direction that substantially intersects the extension direction of the insertion hole 31A (hereinafter this direction will be abbreviated as the 'thickness direction' of the suture fix member 30). The two second arm parts 32B branch from the end of the first arm part 32A to both sides of the wide direction of the first arm part 32A, curve and fold 180 degrees as a hair pin shape, and extend towards the connection part 31. In this structure, housing parts 33, which one part of the suture 10 is hooked, are formed on both sides of the wide direction of the first arm part 32A along the thick direction of the suture fix member 30. Due to the shape of the arm part 32, the housing parts 33 at those two points extend substantially parallel with the first arm part 32A in a front view of the suture fix member 30.

The first arm part 32A and the second arm parts 32B are approximately the same width. This width is shorter than the one side 31B of the connection part 31 along which the first arm part 32A extends. The first arm part 32A extends from an intermediate part in the long direction of the one side 31B. Consequently, regions of the connection part 31 that belong to ends on both sides of the long direction of the side part 31B are formed as protrusions 34 protruding into the housing parts 33. In the knot-formation operation, the protrusions 34 function as hooked suture locking parts for preventing the suture 10 hooked the housing part 33 from escaping from the suture fix member 30.

There are no particular restrictions on the size of the suture fix member 30, which can be set as appropriate after considering the suture position and so on. When the suture fix member 30 is set at a small size of, for example, 1 mm square, it can be manufactured by subjecting a cube with side length of 1 mm formed from, for example, stainless steel or the like, to laser processing, wire electrical discharging machining, cutting, and so on.

An operation when using the ligating device 1 having the configuration described above will be explained, taking as an example a case where a wound is sutured.

The operator inserts the ligating device 1 in the vicinity of treatment target tissue (hereinafter 'target tissue'). An applicator including a sheath, such as that disclosed in Japanese Published Unexamined Application No. H 8-140982 mentioned above, can be used to insert the ligating device 1 in the vicinity of target tissue.

Figure 3:
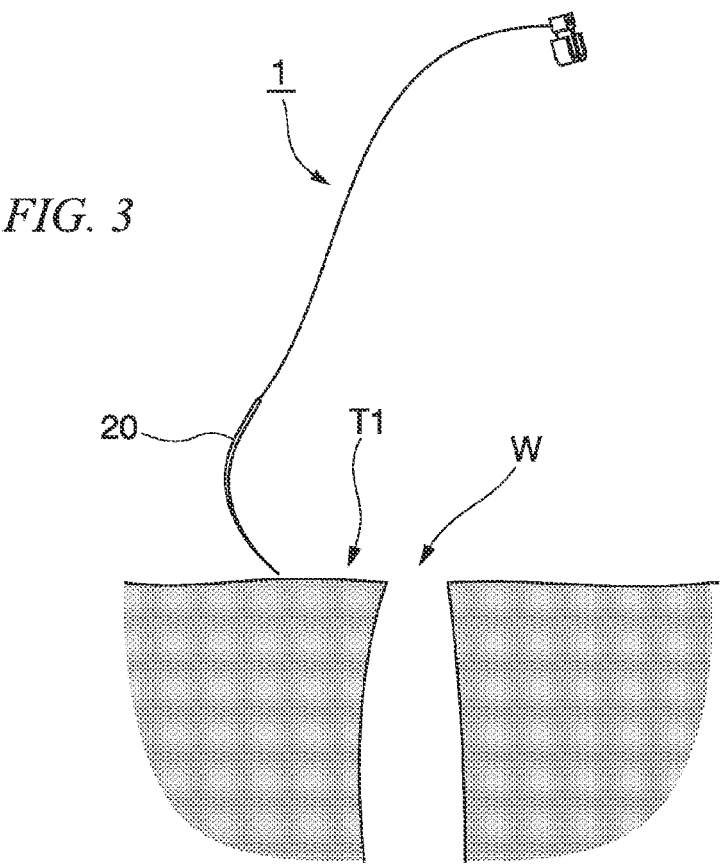
FIG. 3 is a view of an operation when using the tissue ligating device according to the first embodiment of the invention.
Figure 4:
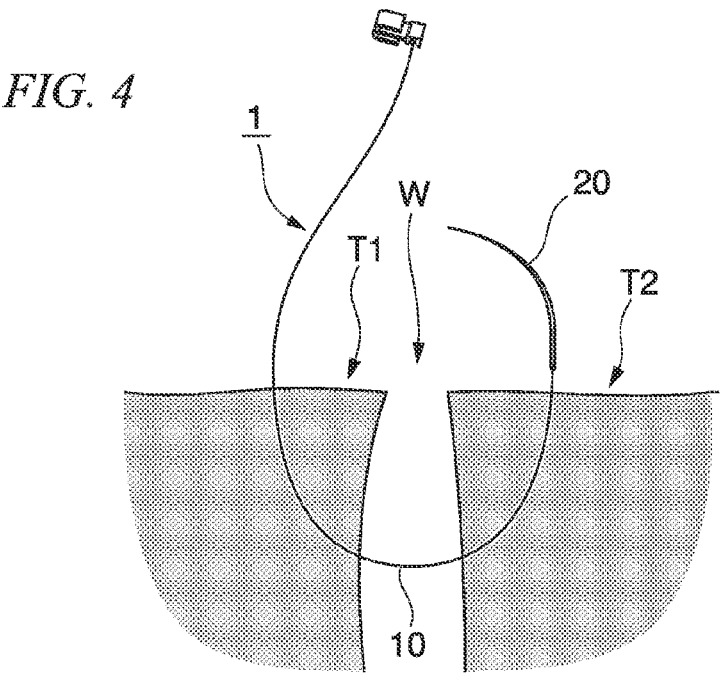
FIG. 4 is a view of an operation when using the tissue ligating device according to the first embodiment of the invention.

After inserting the ligating device 1 into the body, the operator grips the suture needle 20 with a forceps or the like, and, as shown in FIG. 3, applies it to the target tissue T around the wound W. As shown in FIG. 4, the operator clips the wound W, applies the suture needle 20 to the target tissue T2 opposite the target tissue T1, and passes the suture 10 through the target tissue so that the wound W can be sutured.

Figure 5:
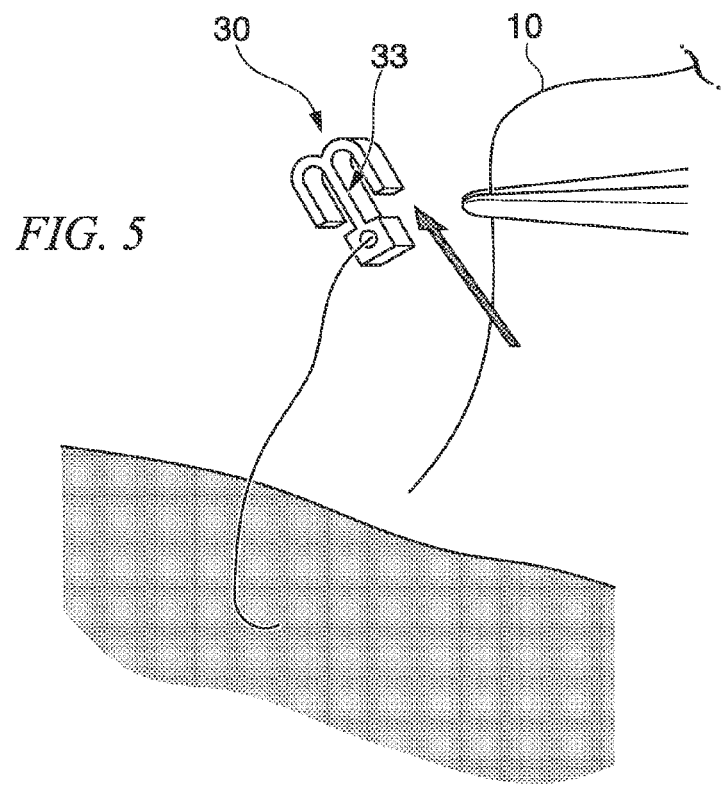
FIG. 5 is a view of an operation when using the tissue ligating device according to the first embodiment of the invention.
Figure 6:
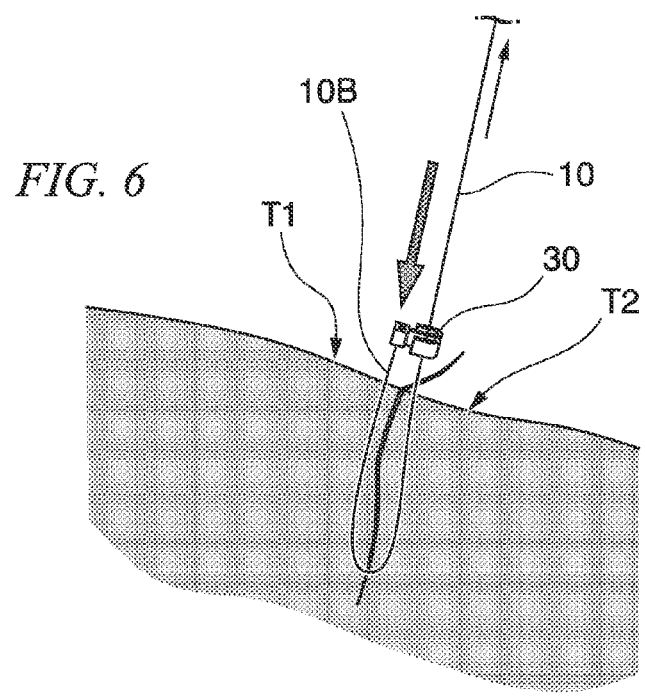
FIG. 6 is a view of an operation when using the tissue ligating device according to the first embodiment of the invention.

As shown in FIG. 5, the operator then grips the suture 10 or the suture needle 20 and passes (hook) one part of the suture 10 through the housing part 33 of the suture fix member 30. The suture 10 can be hooked either of the two housing parts 33. As shown in FIG. 6, when the first end 10A side of the suture 10 is pulled away from the target tissue, the suture fix member 30 connected to the second end 10B approaches the target tissue T1 and presses against it. Also, the suture 10 passing the target tissue is drawn tight, pulling the target tissues T1 and T2 closer to each other.

In the above operation, due to the elasticity or due to the application of an external force, the suture 10 sometimes moves in a direction of escaping (disengaging) from the housing part 33. However, as shown in FIG. 7B, this movement of the suture 10 described above is obstructed by the protrusion 34 protruding into the housing part 33. This favorably prevents the suture 10 from disengaging from the housing part 33 and escaping from the suture fix member 30. That is, in this ligating device, whether the suture 10 has elasticity or not, it can be prevented from disengaging from the housing part 33.

Figure 7A:
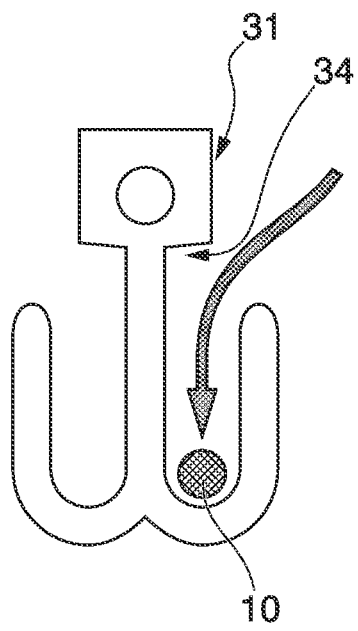
FIG. 7A is a view of the behavior of a suture being inserted into a suture fix member of the tissue ligating device according to the first embodiment of the invention.
Figure 7B:
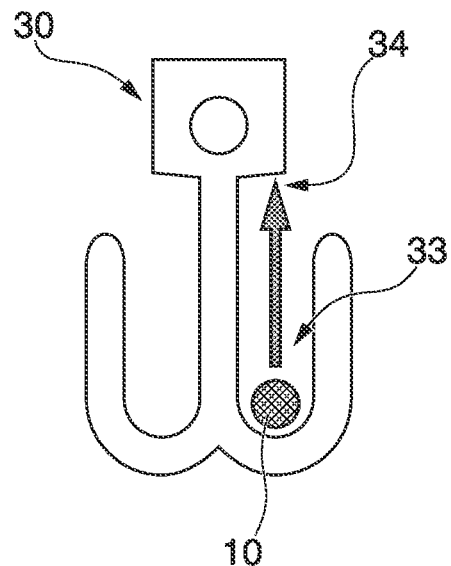
FIG. 7B is a view of the behavior of a suture being inserted into a suture fix member of the tissue ligating device according to the first embodiment of the invention.

When the suture 10 is inserted into the housing part 33, as shown in FIG. 7A, the suture 10 passes beside the connection part 31 and is inserted into the housing part 33 from the outer side of the wide direction of the second arm part 32B. Therefore, the protrusion 34 hardly obstructs the hooking operation of passing the suture 10 through the housing part 33.

Figure 8:
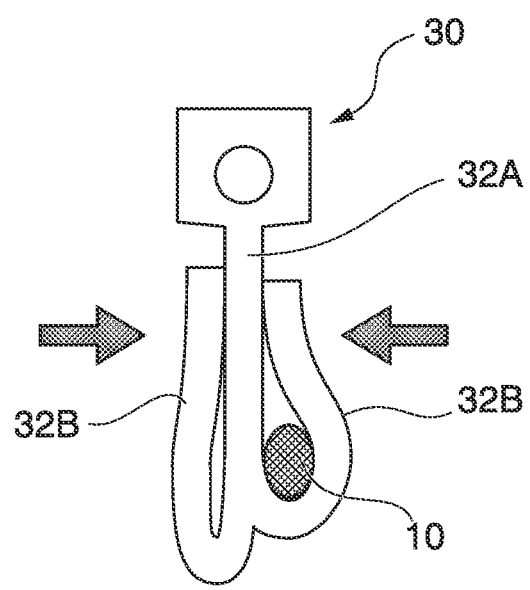
FIG. 8 is a view of an operation of fixing a suture and a suture fix member.

When the operator has drawn the suture 10 sufficiently tight, the operator uses a forceps or the like to grip the first arm part 32A and the second arm parts 32B, making the second arm parts 32B deform and thereby securing the suture 10 and the suture fix member 30 as shown in FIG. 8.

Figure 9:
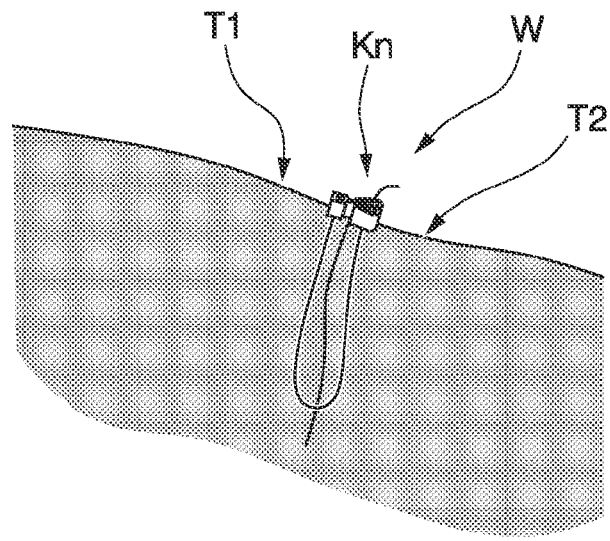
FIG. 9 is a view of a tissue ligating device according to the first embodiment of the invention after a knot has been formed.

Then, the point where the suture 10 and the suture fix member 30 are secured functions as a suture knot Kn, and, as shown in FIG. 9, the target tissue T1 and the target tissue T2 are sutured so as to cover the wound W. This completes the knot-formation operation using the ligating device 1. In forming the knot Kn, the suturing can be done more reliably by applying tension while pulling the suture 10.

After the knot Kn has been formed, the operator cuts off the excess part of the suture 10, and collects the suture needle 20 and the suture 10 that was cut off from outside the body cavity. In the case of a large wound W or the like, the operator continues by introducing a new ligating device 1 and repeating the knot-formation operation described above. Then, the operator ends the procedure when the operator has completely sutured the wound W.

The point where the suture 10 and the suture fix member 30 are secured is actually different from a knot made by a method such as a square knot or a granny knot. However, this point functions similarly to a conventional knot made by a surgical method in that it holds the suture 10 applied to the target tissue so that it does not become loose. For that reason, in this invention, this point is termed a knot.

In the ligating device 1 of this embodiment, the suture fix member 30 includes the protrusion 34 protruding into the housing part 33 that the suture 10 is hooked. Therefore, even if the suture 10 moves in a direction of disengaging from the housing part 33 due to elasticity or the like, the protrusion 34 favorably prevents the suture 10 from disengaging from the housing part 33. That is, the protrusion 34 functions as a hooked suture locking part. Therefore, the knot-formation operation can be performed easily and smoothly, and a stable knot can be formed.

In the ligating device 1 of this embodiment, the housing part 33 is formed in the thick direction of the suture fix member 30. Therefore, since the arm part 32 is able to deform sufficiently merely by the application of force from both sides of the wide direction of the arm part 32, the suture fix member 30 and the suture 10 can be easily secured by a simple operation.

In a procedure using an endoscope, a laparoscope, and the like, the space for moving the forceps and the like is limited. The advantageous effects of the ligating device of the invention described above are therefore even more noticeable.

In this embodiment, the external shape of the suture fix member 30 is substantially anchor-shaped, having one first arm part 32A and two second arm parts 32B, and with one part of the connection part 31 being formed as the protrusion 34. However, the shape of the suture fix member can be altered in various ways.

Figures 10A, 10B, 10C:
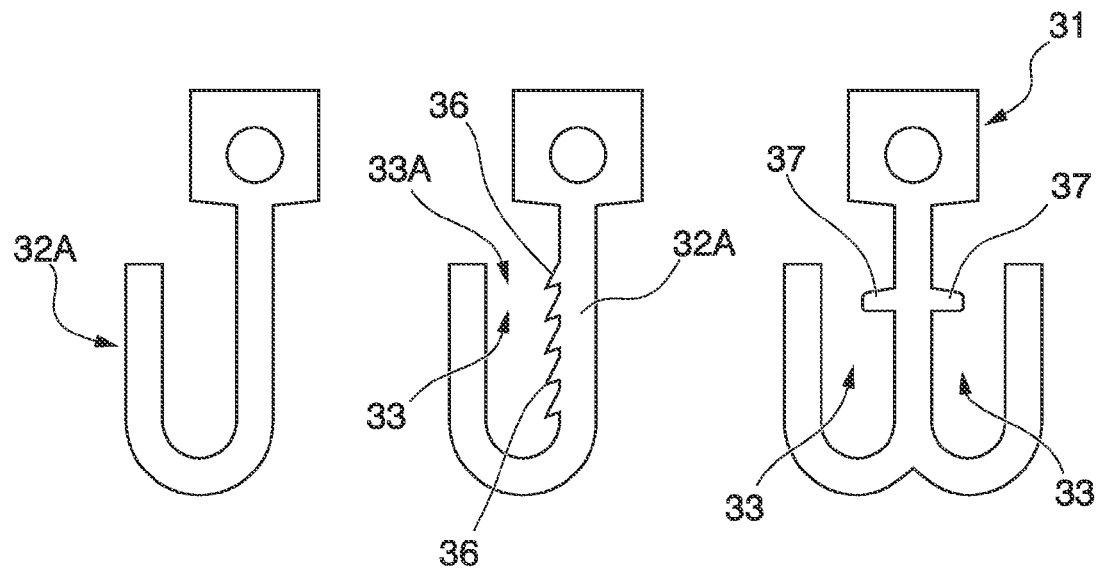
FIG. 10A is a front view of a suture fix member in a modified example of the tissue ligating device according to the first embodiment of the invention.
FIG. 10B is a front view of a suture fix member in a modified example of the tissue ligating device according to the first embodiment of the invention.
FIG. 10C is a front view of a suture fix member in a modified example of the tissue ligating device according to the first embodiment of the invention.

One way of modifying the anchor-shape described above is to provide only one first arm part 32A, as in the modified example shown in FIG. 10A. This makes it easy to reduce the size of the suture fix member, and is convenient for a procedure in a very small region. Also, the region where the first arm part 32A is deformed during knot-formation is smaller, facilitating the deformation operation.

The protrusion can be formed separately from one part of the connection part. For example, as in the modified example of FIG. 10B, a plurality of protrusions 36 can be formed on a side face of the first arm part 32A (or a side face of the second arm part 32B) that forms the inner face of the housing part 33. Alternatively, as in the modified example of FIG. 10C, one protrusion 37 protruding into each housing part 33 can be formed separate from the connection part 31. When the protrusions include parts projecting in a direction away from the opening 33A of the housing part 33 where the suture 10 is introduced into, as is the case with the protrusions 36, the protrusions 36 are unlikely to obstruct the movement of the suture 10 when the suture 10 passes the housing part 33. Therefore, it is possible to favorably obstruct only the movement of the suture 10 in the direction of disengaging from the housing part 33. The protrusions in the modified examples of FIGS. 10B and 10C can also actively obstruct the movement of the suture, while more effectively preventing the suture 10 from disengaging from the housing parts 33.

The suture fix member of this embodiment is not limited to the anchor-shaped configuration described above.

Each of FIGS. 11A to 11I illustrates another modified example of the suture fix member 30.

Figure 11A:
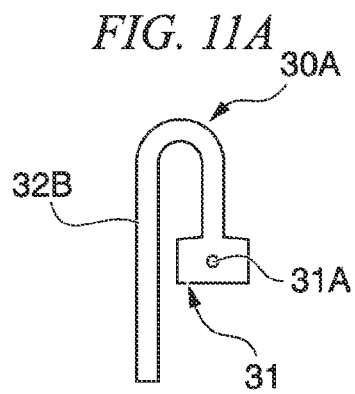
FIG. 11A is a front view of a suture fix member in a modified example of the tissue ligating device according to the first embodiment of the invention.

In the suture fix member 30A shown in FIG. 11A, the second arm part 32B is longer than the first arm part 32A. In this case, the larger region of the connection part 31 functions as a protrusion.

Moreover, since the second arm part 32B functions as a guide when passing the suture 10 through the housing part 33, the knot-formation operation can be performed more easily.

Figure 11B:
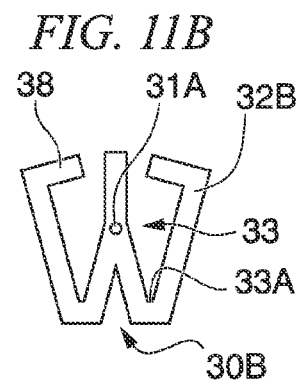
FIG. 11B is a front view of a suture fix member in a modified example of the tissue ligating device according to the first embodiment of the invention.
Figure 11C:
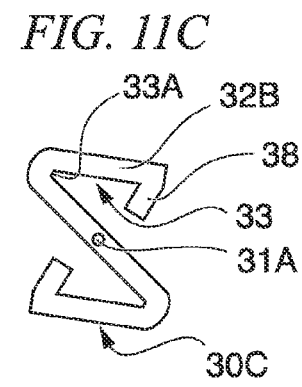
FIG. 11C is a front view of a suture fix member in a modified example of the tissue ligating device according to the first embodiment of the invention.

In the suture fix members 30B and 30C shown respectively in FIGS. 11B and 11C, the second arm parts 32B are folded at an acute angle so that the housing parts 33 have angular parts 33A.

The protrusions 38 are provided at the ends of the second arm parts 32B. In this instance, the behavior of the suture 10 during the knot-formation operation is stabilized by drawing and tightening the suture 10 in a direction of pushing it against the angular part 33A when the suture 10 is hooked the housing part 33. Moreover, since the suture 10 being directed into the angular part 33A is not easily loosen, the knot Kn can be formed more stably.

Figure 11D:
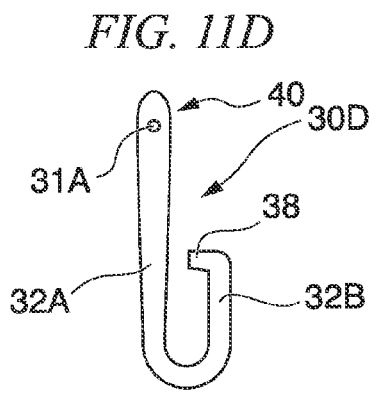
FIG. 11D is a front view of a suture fix member in a modified example of the tissue ligating device according to the first embodiment of the invention.
Figure 11E:
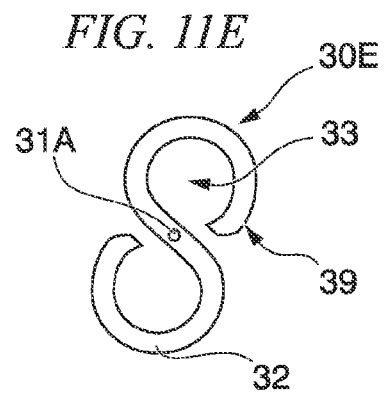
FIG. 11E is a front view of a suture fix member in a modified example of the tissue ligating device according to the first embodiment of the invention.

When the protrusions 38 are formed on the second arm parts 32B, as with the suture fix member 30D shown in FIG. 11D, the connection part 40 can be the same width as the arm parts. In this instance, unlike the suture fix member 30A, the first arm part 32A functions as a guide for the suture 10.

In a suture fix member 30E shown in FIG. 11, the housing parts 33 are substantially circular in front view. Since the housing parts are comparatively large with respect to the suture fix member, this configuration has an advantage that the housing parts are easy to confirm visually. At the arm part 32, the interface between the first arm part and the second arm part is unclear, and a region of a predetermined length including the tip of the arm part 32 functions as the protrusion 39.

Figure 11F:
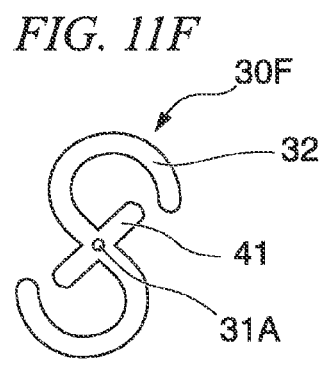
FIG. 11F is a front view of a suture fix member in a modified example of the tissue ligating device according to the first embodiment of the invention.

At this time, as in the suture fix member 30F shown in FIG. 11F, a protrusion 41 can be provided separately from the arm part 32. In this case, an opening for passing the suture through the housing part is formed further away from insertion hole 31A than the suture fix member 30E. This can prevent problems such as the suture becoming entangled, or the operator mistaking the side for drawing the suture during in the knot-formation operation.

Figure 11G:
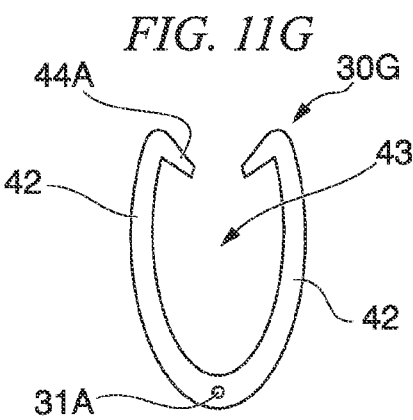
FIG. 11G is a front view of a suture fix member in a modified example of the tissue ligating device according to the first embodiment of the invention.
Figure 11H:
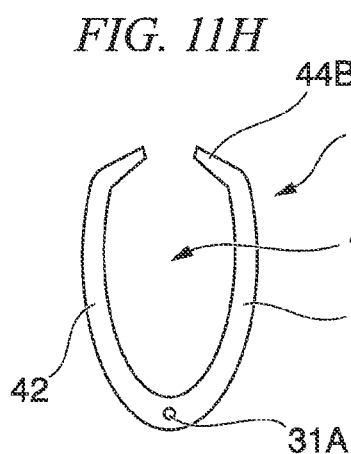
FIG. 11H is a front view of a suture fix member in a modified example of the tissue ligating device according to the first embodiment of the invention.
Figure 11I:
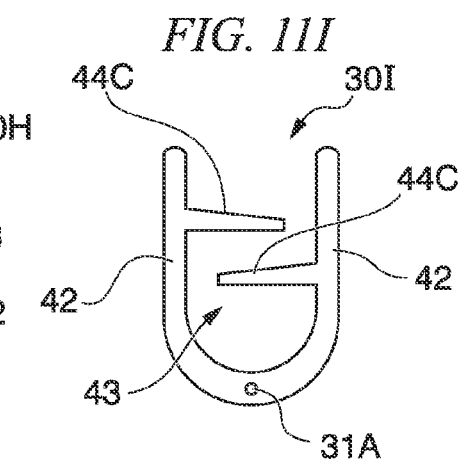
FIG. 11I is a front view of a suture fix member in a modified example of the tissue ligating device according to the first embodiment of the invention.

In suture fix members 30G, 30H, and 30I shown respectively in FIGS. 11G to 11I, the arm part is not folded back and the second arm part is not provided. In this case, protrusions 44A, 44B, and 44C are provided in a housing part 43 formed between two arm parts 42, thereby favorably preventing the suture 10 from disengaging from the housing part 43.

In each of the suture fix members 30G, 30H, and 30I, instead of aiming for the arm part, the knot can be formed by gripping and crushing the whole suture fix member with a forceps or the like, thereby making the operation easier.

Figure 12A:
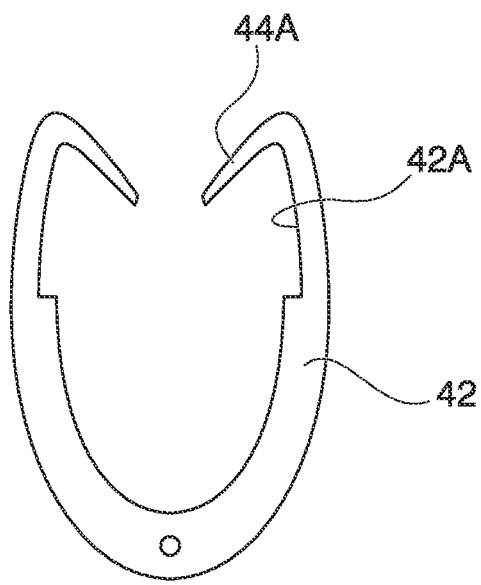
FIG. 12A is a front view of a suture fix member in a modified example of the tissue ligating device according to the first embodiment of the invention.
Figure 12B:
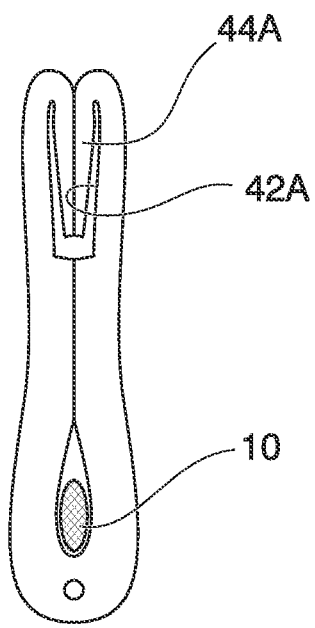
FIG. 12B is a view of a state where a suture fix member is deformed according to the first embodiment of the invention.

When the suture fix member is formed in the shape of the suture fix member 30G, as shown in FIG. 12A, a notch 42A can be formed with a region corresponding to the length of the protrusion 44A from the end of the arm part 42 where the protrusion 44A is formed, such that the width of the arm part 42 decreases. With this configuration, when the suture fix member deforms and is secured to the suture 10, as shown in FIG. 12B, the protrusion 44A is housed in the notch 42A. The suture fix member thus deforms favorably. As a result, the suture and the suture fix member can be secured together more reliably.

Subsequently, a second embodiment of the invention will be explained with reference to FIGS. 13 to 16F.

A ligating device 51 of this embodiment differs from the ligating device 1 described above in regard to the aspect of a suture fix part of the suture fix member. In the explanation below, constitutive elements that are common to those already described above are designated with like reference numerals and will not be repetitiously explained.

Figure 13:
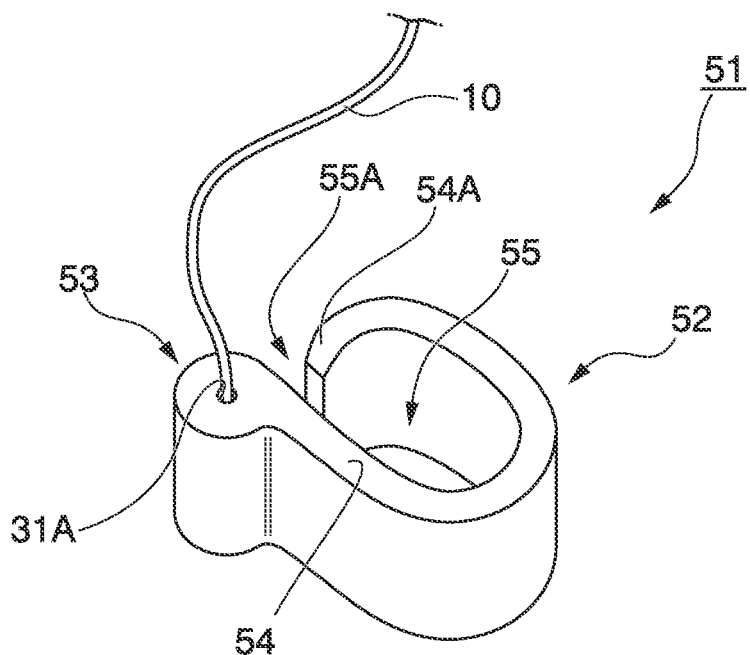
FIG. 13 is a perspective view of a suture fix member and its vicinity in a tissue ligating device according to a second embodiment of the invention.
Figure 14:
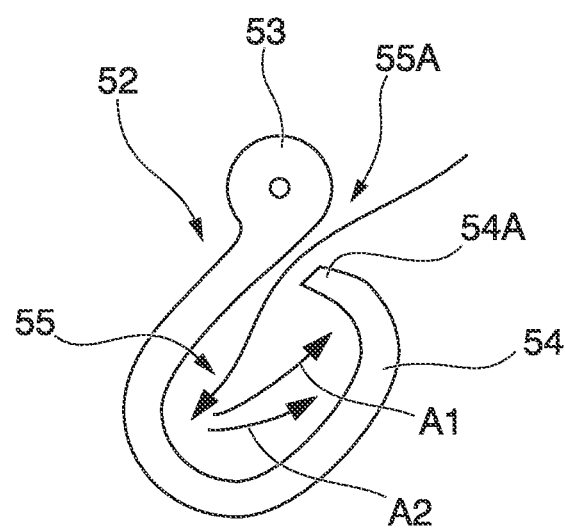
FIG. 14 is an explanatory diagram of a suture stored in a suture fix member in the tissue ligating device according to the second embodiment of the invention.

FIG. 13 is an enlarged view of a suture fix member 52 of the ligating device 51, and its vicinity. A single arm part 54 extends from a connection part 53. The arm part 54 extends while curving in a shape that is substantially oval in a front view of the suture fix member 52. A substantially oval housing part 55 is formed inside the curving arm part 54. The end of the curved arm part 54 extends towards the connection part 53, and forms a constriction part 54A that constricts an opening 55A in the substantially oval housing part 55 that the suture 10 passes through when being housed. In the ligating device 51, this constriction part 54A functions as a hooked suture locking part.

In the ligating device 51 of this embodiment, in a front view of the suture fix member 52, the constriction part 54A constricts the opening 55A, which is one part of the housing part 55. Therefore, even if the suture 10 moves inside the housing 55 due to elasticity or the like, as shown by the arrows A1 and A2 in FIG. 14, the suture 10 strikes against the arm part 54 including the constriction part 54A, thereby reducing the probability that the suture 10 will pass the opening 55A and disengage from the housing part 55. Therefore, as in the ligating device 1, the suture 10 can be favorably prevented from disengaging from the housing part 55 during the knot-formation operation.

In the ligating device 51 of this embodiment, the faces of the connection part 53 and the arm part 54 formed opposite the constriction part 54A with the opening 55A therebetween are flat. Therefore, when inserting the suture 10 into the housing part 55, the suture 10 follows the connection part 53 and the arm part 54, enabling the suture 10 to move smoothly into the housing part 55.

As in the first embodiment, the suture fix member including the constriction part as a suture fix part is not limited to the shape of the suture fix member 52 described above, and can be formed in various aspects.

Figure 15A:
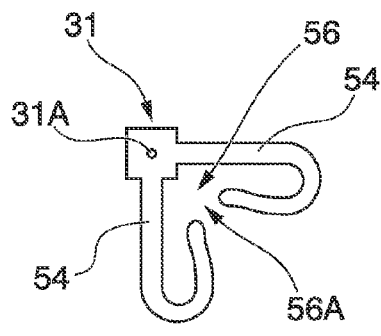
FIG. 15A is a front view of a suture fix member in a modified example of the tissue ligating device according to the second embodiment of the invention.
Figure 15B:
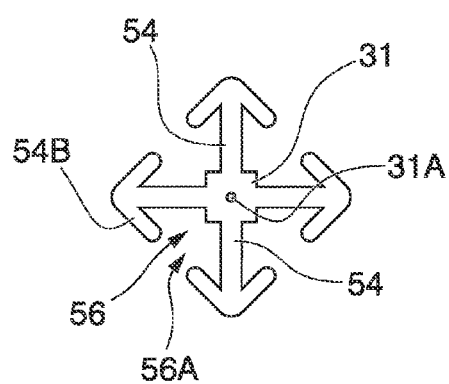
FIG. 15B is a front view of a suture fix member in a modified example of the tissue ligating device according to the second embodiment of the invention.

FIG. 15A and FIG. 15B are modified examples based on a substantially anchor-shaped suture fix member such as the suture fix member 30. In the modified example of FIG. 15A, two arm parts 54 extend from the connection part 31. In the modified example of FIG. 15B, four arm parts 54 extend from the connection part 31.

In each of the modified examples shown in FIGS. 15A and 15B, two adjacent arm parts form a housing part 56 that is substantially triangular in front view. In the modified example of FIG. 15A, the tip-end side of the arm part 54 functions as a constriction part that constricts the opening 56A of the housing part 56. In the modified example of FIG. 15B, a protrusion 54B provided on the arm part 54 functions as a constriction part that constricts the opening 56A of the housing part 56.

When housing parts are provided at a plurality of points, the dimension of the suture fix member increases slightly. However, when passing the suture through the housing part, there will be fewer cases that require the delicate operation of deciding to aim for a specific arm part of the suture fix member and then moving one part of the suture accordingly. This makes the knot-formation operation easier to perform.

FIGS. 16A to 16F each illustrate other modified examples of a suture fix member having a constriction part. As in a suture fix member 52A shown in FIG. 16A, the suture fix member of this embodiment can include a bent arm part 57. in this instance, it is possible to ensure a certain amount of freedom in regard to the direction of applying a force for making the arm part 57 deform, and it is possible to make the knot-formation operation easier to perform. Furthermore, as in a suture fix member 52B shown in FIG. 16B, an arm part 59 can bend at an acute angle such that the housing part 58 has an angular part 58A. A suture fix member 52C shown in FIG. 16C includes an arm part 60 having a bend angle that is middle of an angle of the suture fix member 52A and an angle of the suture fix member 52B. The suture fix members 52B and 52C are advantageous in that they deform more easily than the suture fix member 52A, and they make the knot-formation operation easier to perform.

Figure 16A:
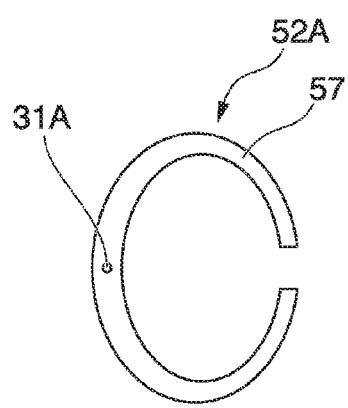
FIG. 16A is a front view of a suture fix member in a modified example of the tissue ligating device according to the second embodiment of the invention.
Figure 16B:
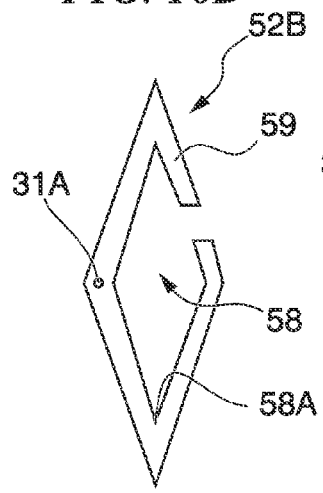
FIG. 16B is a front view of a suture fix member in a modified example of the tissue ligating device according to the second embodiment of the invention.
Figure 16C:
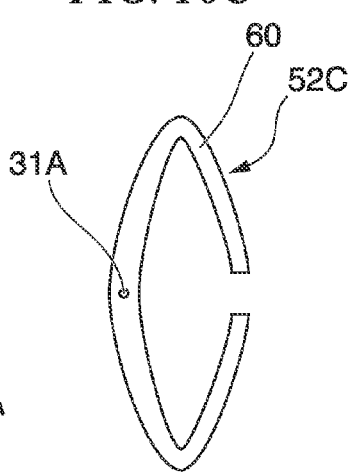
FIG. 16C is a front view of a suture fix member in a modified example of the tissue ligating device according to the second embodiment of the invention.
Figure 16D:
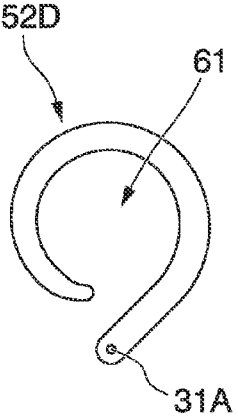
FIG. 16D is a front view of a suture fix member in a modified example of the tissue ligating device according to the second embodiment of the invention.
Figure 16E:
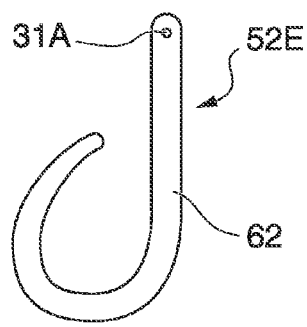
FIG. 16E is a front view of a suture fix member in a modified example of the tissue ligating device according to the second embodiment of the invention.

In addition, as in the suture fix member 52D shown in FIG. 16D, a housing part 61 can be formed in a shape that is substantially circular in front view. Also, as in the suture fix member 52E shown in FIG. 16E, one part of the arm part 62 can be formed in a linear shape.

Figure 16F:
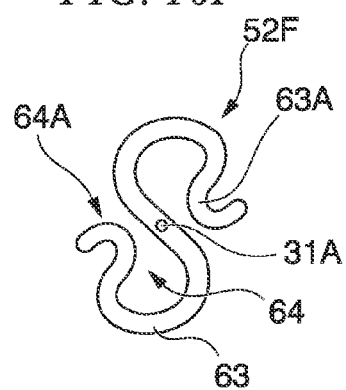
FIG. 16F is a front view of a suture fix member in a modified example of the tissue ligating device according to the second embodiment of the invention.

As in the suture fix member 52F shown in FIG. 16F, the arm part 63 can include a constriction part 63A that constricts a part of the housing part that is not the opening. In this instance, since it is possible to make wider the opening 64A in the housing part 64, the suture 10 can be passed easily. Moreover, the housed suture 10 can be favorably prevented from disengaging from the housing part 64.

Subsequently, a third embodiment of the invention will be explained with reference to FIGS. 17 to 19G. A ligating device 71 of this embodiment differs from those of the embodiments described above in regard to the shape of the housing part.

Figure 17:
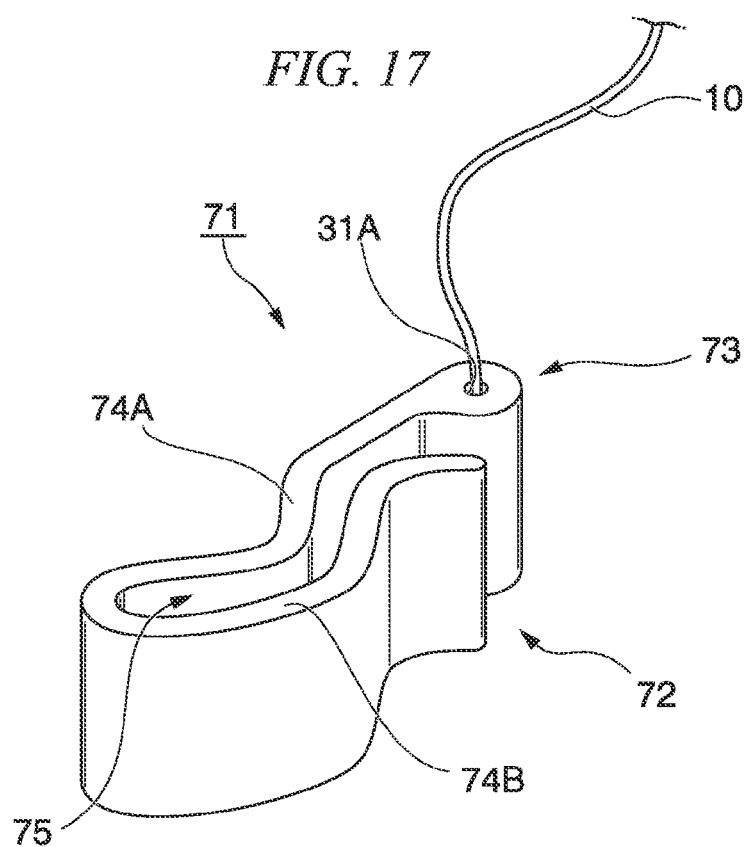
FIG. 17 is a perspective view of a suture fix member and its vicinity of a tissue ligating device according to a third embodiment of the invention.

FIG. 17 is a perspective view of a suture fix member 72 of the ligating device 71, and its vicinity. In the suture fix member 72, a first arm part 74A and a second arm part 74B extending from a connection part 73 are formed so that they bend in a front view of the suture fix member 72. As a result, a housing part 75 formed between the first arm part 74A and the second arm part 74B is bent in a front view of the suture fix member 72.

In the embodiments of this invention, 'bent' denotes a state where a line connecting a deepest part of the housing part, where the distance in alignment with form of the housing part from an opening in the housing part through which the suture enters is greatest, to the opening cannot be drawn so that, when viewed from at least one direction, the line does not make contact with the arm parts that define the housing part.

Figure 18:
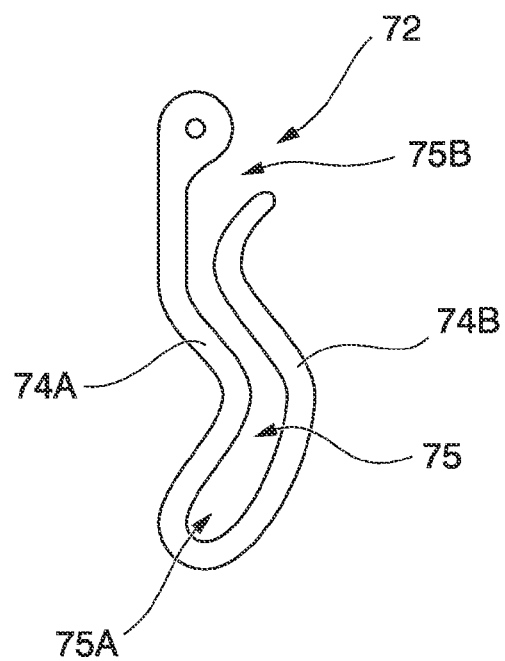
FIG. 18 is a front view of a suture fix member in the tissue ligating device according to the third embodiment of the invention

For example, in the suture fix member 72, as shown in FIG. 18, the deepest part 75A of the housing part 75 is located near the interface between the first arm part 74A and the second arm part 74B. In a front view of the suture fix member 72, a line connecting the deepest part 75A to the opening 75B cannot be formed without making contact with the first arm part 74A and the second arm part 74B. That is, the housing part 75 of the suture fix member 72 bends in a front view of the suture fix member 72.

In the ligating device 71 configured as described above, when passing the suture 10 into the housing part 75, since the suture 10 follows the shape of the first arm part 74A or the second arm part 74B, it can easily be moved to the vicinity of the deepest part 75A.

The movement of the suture 10 as it attempts to return to a linear shape due to its elasticity or the like, is generally a substantially linear movement in one direction. Therefore, whichever direction it moves in, the suture 10 that has hooked the bent housing part 75 will make contact with either the first arm part 74A or the second arm part 74B. It is thus practically impossible for the suture 10 to reach the opening 75B only by the substantially linear movement mentioned above.

Therefore, due to its overall shape, the bending housing part 75 functions as a hooked suture locking part, and can favorably prevent the suture 10 from escaping from the suture fix member 72.

In this embodiment, the specific bending shaped of the housing part can be varied.

The suture fix member 72A shown in FIG. 19A is a modified example including two housing parts shaped similar to the housing part 75, and has line symmetry in front view. The suture fix member 72A has a substantially anchor shape similar to that of the suture fix member 30 of the first embodiment, so that a suture passed through the housing part is more unlikely to become disengaged than from the suture fix member 30. Since two housing parts are provided, the suture can easily be passed. Moreover, the suture fix member 72A includes a release hole 77 for reducing the thickness of the first arm part 76A. This enables the housing part to be easily deformed at the same time as the housing part is being bent. Moreover, there is a comparatively high degree of freedom in regard to the direction of deforming the housing part, making the knot-formation operation easier.

Suture fix members 72B and 72C shown respectively in FIGS. 19B and 19C include bend points where the bend angle of the housing part is approximately 90 degrees. The remaining regions of the housing parts of the suture fix members 72B and 72C are substantially linear. This configuration enables the suture 10 to be passed easily through the housing part.

Suture fix members 72D and 72E shown respectively in FIGS. 19D and 19E include housing parts having comparatively complex shapes with a plurality of bend points. The bend points of the housing part can be formed smoothly curving shape like those in FIG. 19D, or the bend points of the housing part can be formed so that the bend points include angular parts like those in FIG. 19E. The bend points can be formed so that the shapes in FIGS. 19D and 19E can also be combined. The suture fix members 72D and 72E ensure that the suture is more unlikely to become disengaged from the housing part.

As in the suture fix member 72F shown in FIG. 19F, the configuration can be one where the outer shape of the suture fix member does not bend, and only the housing part bends. In this case, since the outer face of the suture fix member is flat, a force for making the suture fix member deform can be applied stably. Therefore, it is possible to form the knot efficiency.

As in the suture fix member 72G shown in FIG. 19G, the housing part can be shaped like a spiral in front view. In this instance, similar to the suture fix members 72D and 72E, a suture passed through the housing part more unlikely to become disengaged.

Subsequently, a fourth embodiment of the invention will be explained with reference to FIGS. 20A to 21C.

Figure 20A:
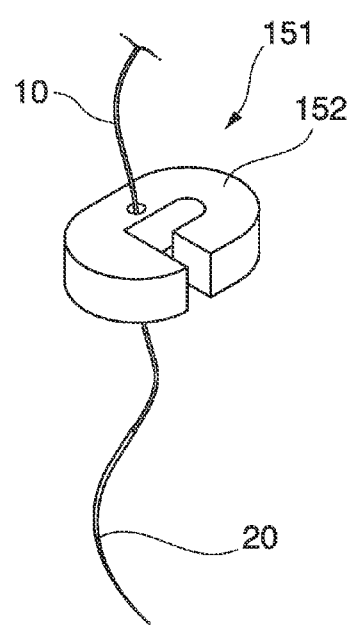
FIG. 20A is a perspective view of a suture fix member and its vicinity in a tissue ligating device according to a fourth embodiment of the invention.
Figure 20B:
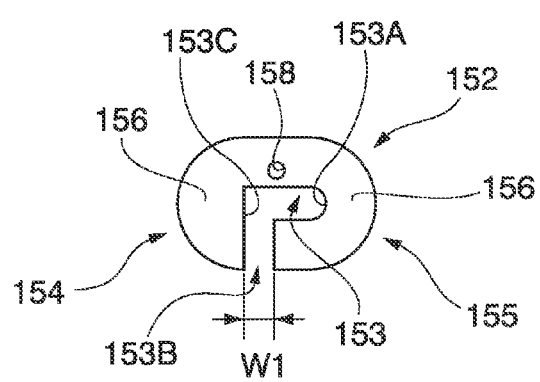
FIG. 20B is a front view of a suture fix member in the tissue ligating device according to the fourth embodiment of the invention

FIG. 20A is an enlarged perspective view of a suture fix member 152, and its vicinity, of a ligating device 151 of this embodiment. As shown in FIG. 20B, the suture fix member 152 is substantially oval in front view. A housing part 153 opens in the short diameter direction of the oval, and bends substantially in an L-shape.

In a front view of the suture fix member 152, a first arm part 154 and a second arm part 155 that define the shape of the housing part 153 include wide parts 156 which are larger than the dimension W1 of the wide direction (the direction orthogonal to the extension direction) of the housing part 153.

The operation when using the ligating device 151 is broadly similar to that of the ligating devices of the embodiments described earlier: the suture 10 is positioned near a deepest part 153A of the housing part 153, which is then deformed to form a knot Kn.

As in the embodiments described above, the ligating device 151 of this embodiment enables the knot-formation operation to be performed easily and smoothly, and enables the knot to be formed stably.

In the ligating device of this embodiment, as in the third embodiment, the housing part 153 is being bent, and the bending state functions as a hooked suture locking part. The region of the housing part 153 in which the suture 10 is actually housed is the region on the deepest part 153A side from the bent intermediate part. An inner wall 153C opposite the deepest part 153A on the opening 153B side from the intermediate part is especially effective in preventing disengagement, and practically functions as a hooked suture locking part.

In the ligating device of this embodiment, since the first arm part 154 and the second arm part 155 include the wide parts 156, even if the dimension of the suture fix member 152 is small, the operator can easily recognize the whole suture fix member as a lump, thus ensuring that the ligating device is still easy to perceive visually.

Also, since the ligating device of this embodiment is substantially oval in front view, it can be efficiently manufactured using a column-shaped material that is oval in cross-section. That is, it can be efficiently manufactured by forming the shape of the housing part in the long direction of the column-shaped material by wire electrical discharge machining or the like, and then slicing the column-shaped material in its diameter direction.

While this embodiment describes an example where the suture fix member is substantially oval in front view, it can be circular, elliptical, or multi-angular in front view instead. Even if the suture fix member is formed in these shapes, it is possible to ensure good visual perceptibility by wide parts being provided on the first arm part and the second arm part, and to be efficiently manufactured using a column-shaped material having a cross-sectional shape that matches the shape of the ligating device in front view.

Figure 21A:
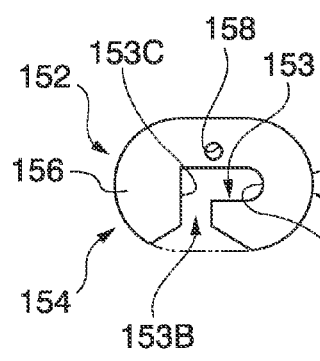
FIG. 21A is a front view of a suture fix member in a modified example of the tissue ligating device according to the fourth embodiment of the invention.

As in the modified example of FIG. 21A, the width of the opening 153B of the housing part 153 can be made wider than at the other points, whereby the suture can be introduced more easily into the housing part. This kind of processing can easily be performed using wire electrical discharge machining or the like mentioned above.

Figure 21B:
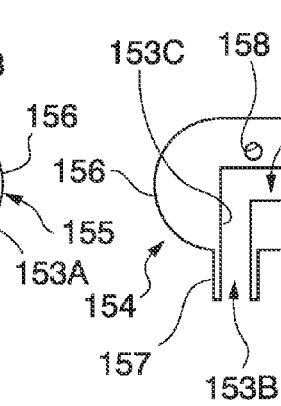
FIG. 21B is a front view of a suture fix member in a modified example of the tissue ligating device according to the fourth embodiment of the invention.

As in FIG. 21B, the opening 153B can be provided with a protrusion 157. This configuration increases the area of the suture fix member when viewed from the side, and thus enhances its visual perceptibility in side view. Furthermore, the position of the opening 153B is easier to ascertain, and the operation of introducing a suture into the housing part becomes easier.

Figure 21C:
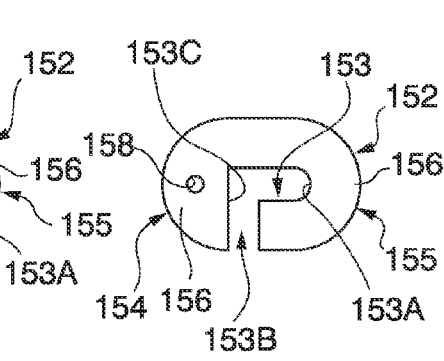
FIG. 21C is a front view of a suture fix member in a modified example of the tissue ligating device according to the fourth embodiment of the invention.

Moreover, as shown in FIG. 21C, the connection 158 can be provided at a different position.

While embodiments of the invention have been described above, the technical scope of the invention is limited not to these embodiments. Various additions, omissions, substitutions, and other modified examples can be made, and the constituent elements of the embodiments can be combined together, without departing from the main points of the invention.

For example, in each of the above embodiments, the example described is one where a hooked suture locking part is provided by forming at least one part of the suture fix member in a predetermined shape. However, instead of this configuration, the hooked suture locking part can be provided by attaching an another member. Several examples of such a modified example will be explained.

Figure 22:
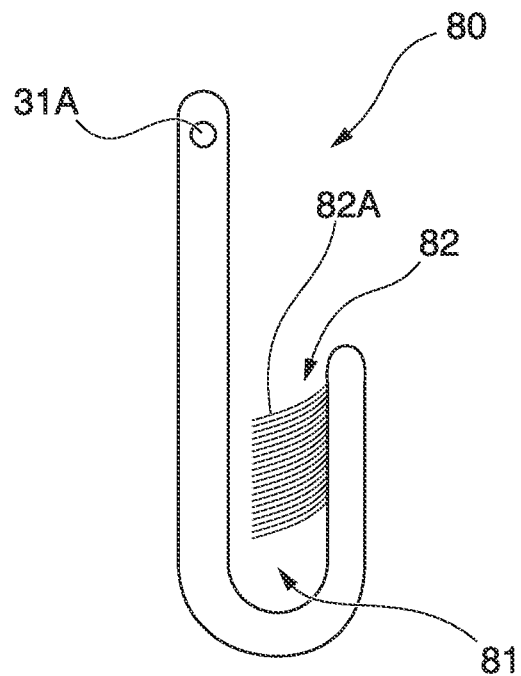
FIG. 22 is a front view of a suture fix member in a tissue ligating device in a modified example of the invention.

A suture fix member 80 shown in FIG. 22 includes a brush-shaped hooked suture locking part 82 in which a plurality of hair-like members 82A are attached to the inner face of a housing part 81.

Figure 23:
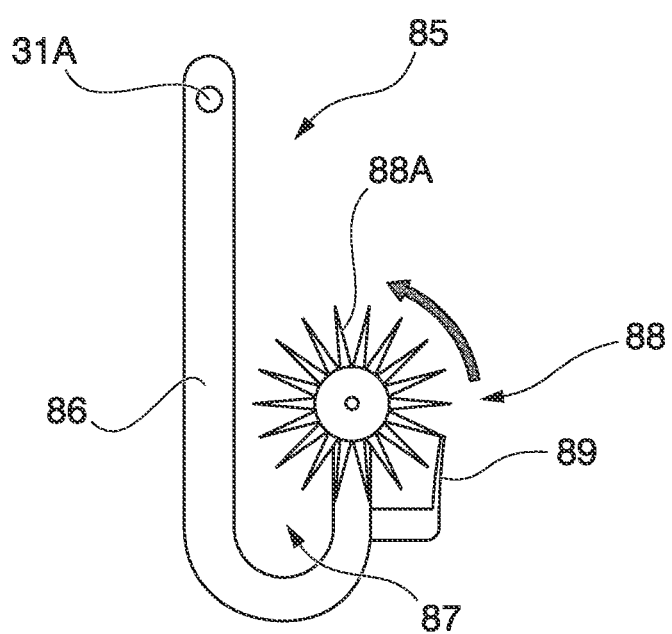
FIG. 23 is a front view of a suture fix member in a tissue ligating device in a modified example of the invention.

In a suture fix member 85 shown in FIG. 23, a wheel 88 with a plurality of protrusions 88A is rotatably attached at a position that is near an opening in a housing part 87 of an arm part 86. A stopper 89 with a constant elasticity is attached to the arm part 86, and interferes with the protrusions 88A. The wheel 88 can rotate in a direction of inducing a suture into the housing part 87 (the direction indicated by the arrow in FIG.

23), and cannot rotate in the reverse direction. Therefore, the wheel 88 prevents the suture from moving in a direction of disengaging from the housing part 87. That is, in the suture fix member 85, the wheel 88 and the stopper 89 constitute a hooked suture locking part.

Figure 24:
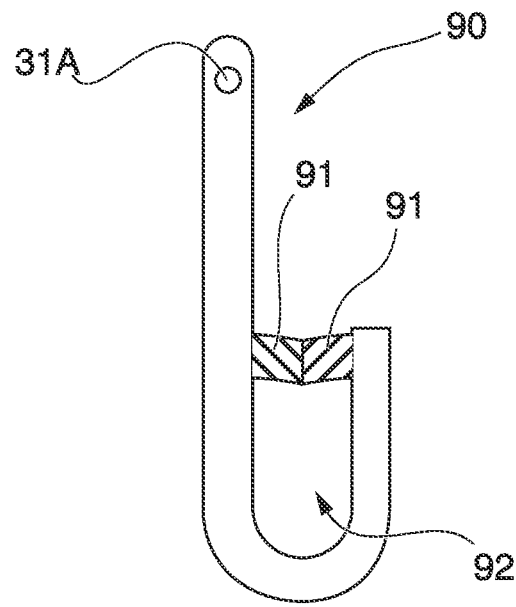
FIG. 24 is a front view of a suture fix member in a tissue ligating device in a modified example of the invention.

FIG. 24 illustrates a suture fix member 90 including elastic members 91 of rubber or the like, which are firmly attached such as to cover a housing part 92 in front view. Since the elastic members 91 elastically deform, the suture 10 can be passed into the housing part 92 using a forceps or the like. On the other hand, with only the movement of the suture 10 attempting to return to its linear shape, sufficient force cannot be obtained and the elastic members 91 are unlikely to deform. The elastic members 91 thus function as hooked suture locking parts.

Figure 25:
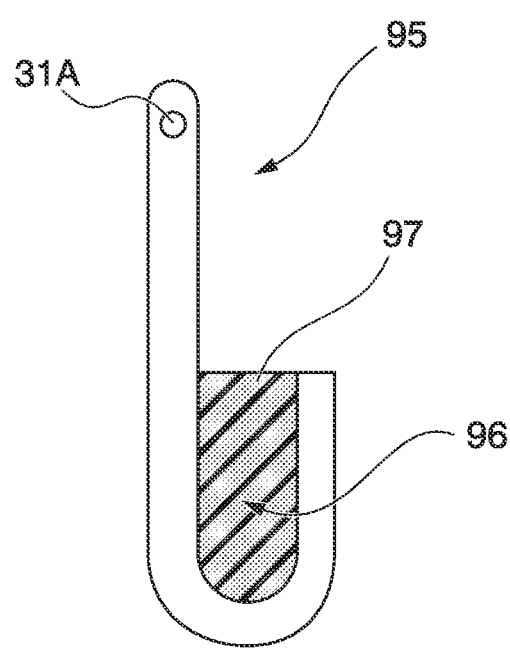
FIG. 25 is a front view of a suture fix member in a tissue ligating device in a modified example of the invention.

FIG. 25 illustrates a suture fix member 95 including a gel-like disengagement-prevention material 97 having constant viscosity arranged inside a housing part 96. The suture 10 passed through the housing part 96 generates friction with the disengagement-prevention material 97, thereby favorably suppressing the disengagement of the suture from the housing part 96.

This modified example includes a hooked suture locking part constituted by the disengagement-prevention material 97, which does not correspond to any of the embodiments described above. If the disengagement-prevention material 97 has high viscosity, a resistant force is generated when tightening the suture in the knot-formation operation, and this obstructs the operation.

Figure 26A:
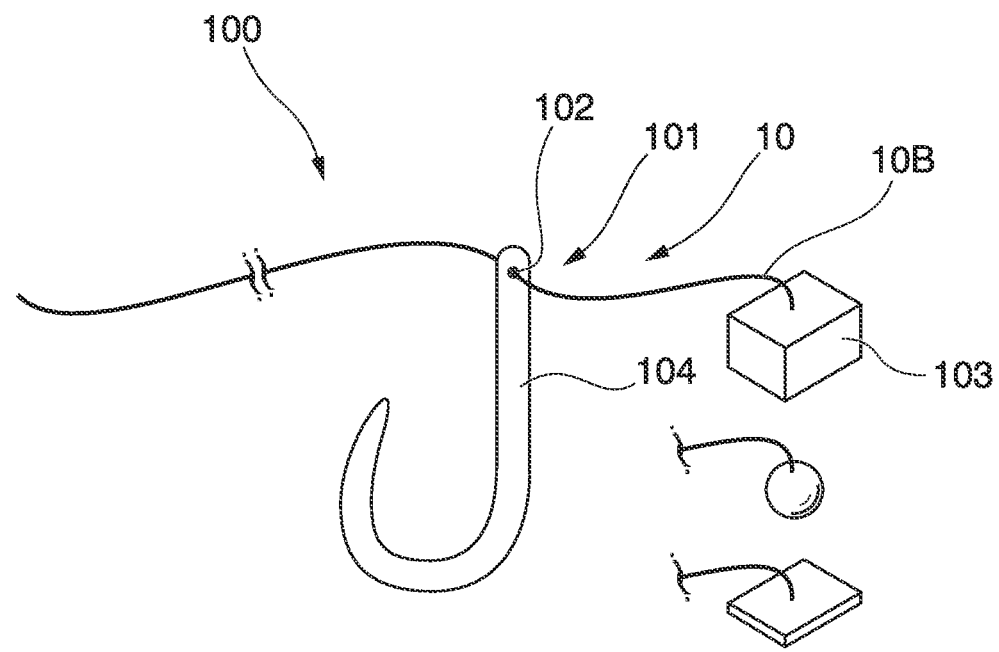
FIG. 26A is a view of a tissue ligating device in a modified example of the invention.
Figure 26B:
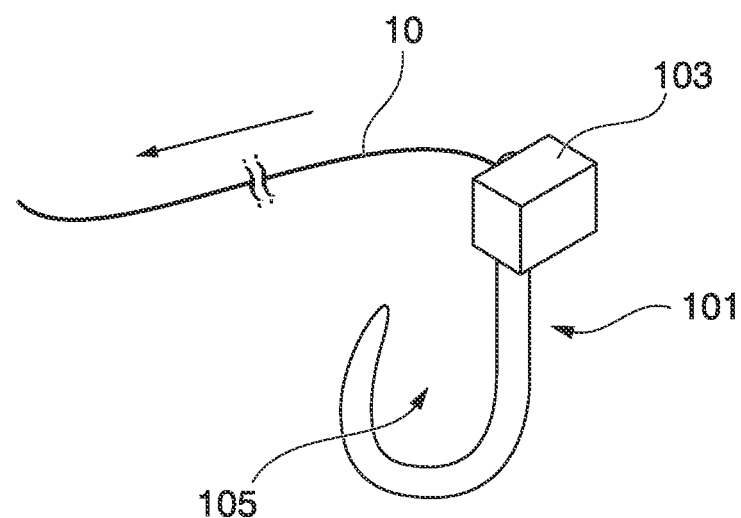
FIG. 26B is a view of a tissue ligating device in a modified example of the invention.

The hooked suture locking part need not be provided in one piece with the suture fix member. In a ligating device 100 in the modified example shown in FIG. 26A, an insertion hole 102 formed with a suture fix member 101 penetrates the suture fix member 101. A disengagement-prevention member 103 is connected and secured to a second end 10B of a suture 10 hooked the insertion hole 102. At least one part of the disengagement-prevention member 103 is larger than the width of arm part 104. When the operator applies the suture 10 to a target tissue and pulls the suture 10, as shown in FIG. 26B, the disengagement-prevention member 103 contacts the suture fix member 101 and obstructs the movement of the suture 10 in the housing part 105. That is, the disengagement-prevention member 103 functions as a hooked suture locking part.

There are no particular restrictions on the shape of the disengagement-prevention member 103, which need only be shaped so that at least one part is larger than the arm part 104. As shown in FIG. 26A, the disengagement-prevention member 103 can be cubic, spherical, plate-shaped, or the like.

In this modified example, the suture fix member 101 and the suture 10 are attached so that they can slide.

In the ligating device according to this embodiment of the invention, the suture and the suture fix member can be attached in the manner described above.

Moreover, the hooked suture locking part can be provided in the thick direction of the suture fix member.

Figure 27A:
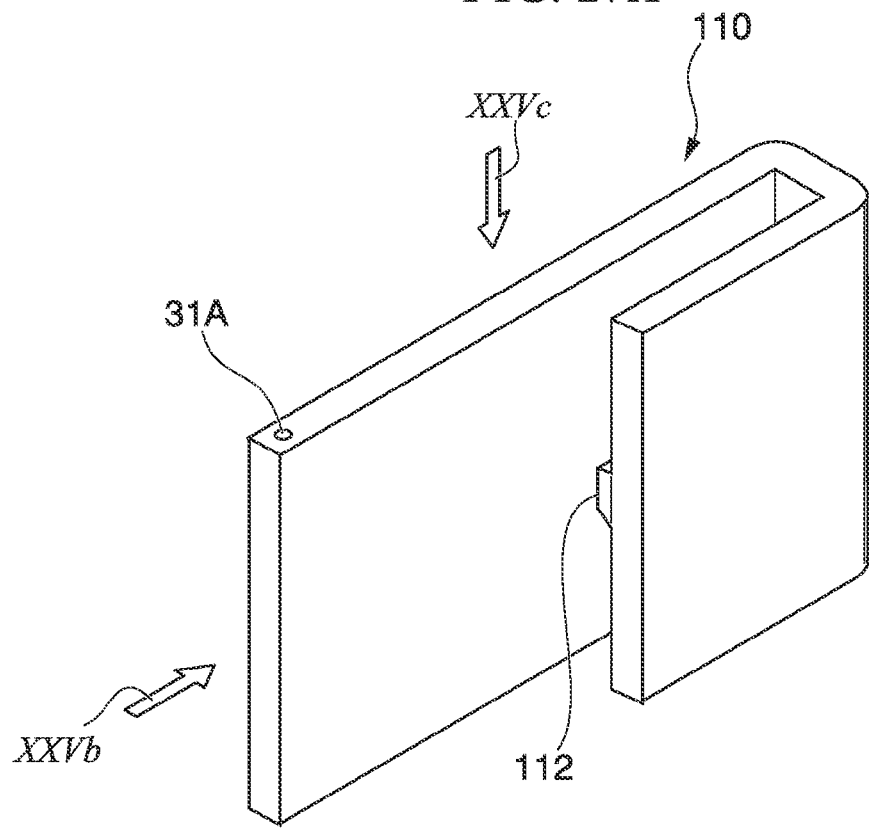
FIG. 27A is a view of a suture fix member in a tissue ligating device in a modified example of the invention.
Figure 27B:
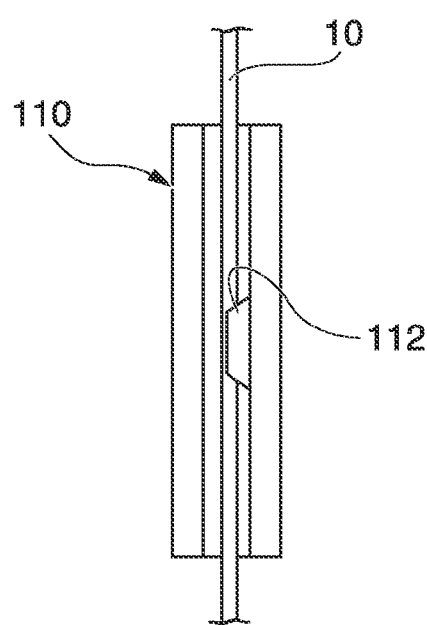
FIG. 27B is a view of a suture fix member in a tissue ligating device in a modified example of the invention.
Figure 27C:
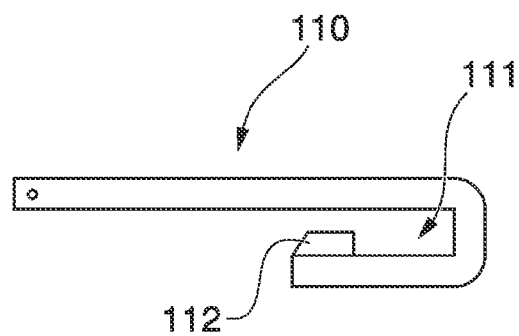
FIG. 27C is a view of a suture fix member in a tissue ligating device in a modified example of the invention.

FIGS. 27A to 27C are examples of a suture fix member in which the protrusion is formed with only one part of the suture fix member in the thickness direction. FIG. 27B is a view along the arrow XXVb of FIG. 27A. FIG. 27C is a view along the arrow XXVc of FIG. 27A. The basic shape of a housing part 111 of a suture fix member 110 is substantially linear in a front view of the suture fix member 110, and a protrusion 112 protrudes into the housing part 111 only in one part of the thick direction of the suture fix member 110.

Figure 28A:
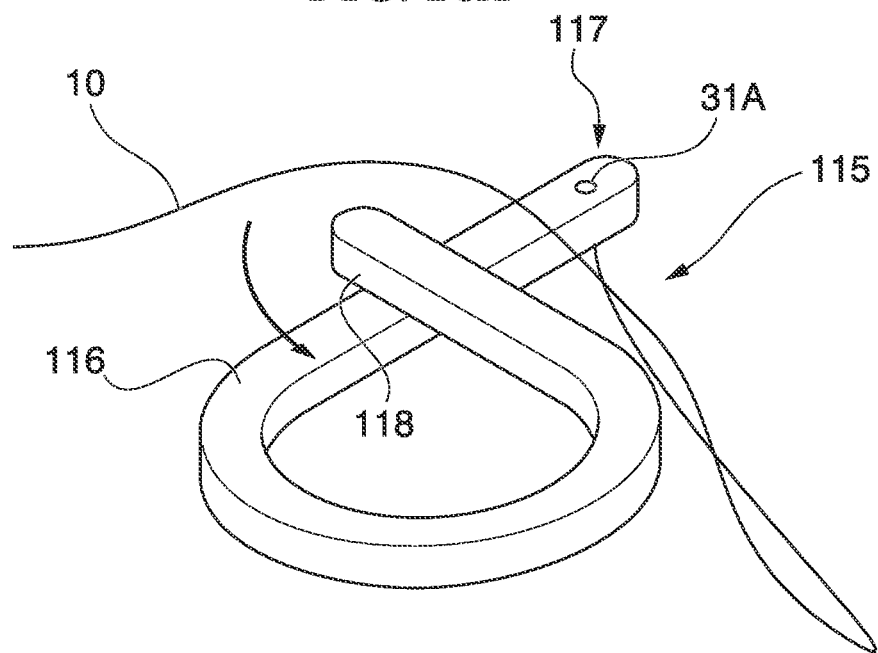
FIG. 28A is a view of a suture fix member and its vicinity in a tissue ligating device in a modified example of the invention.
Figure 28B:
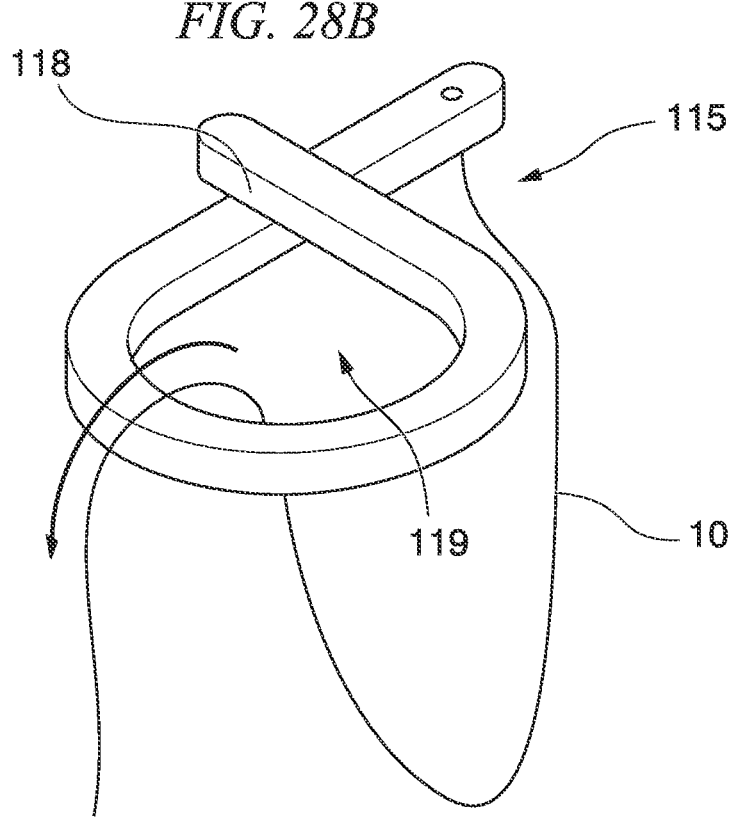
FIG. 28B is a view of a suture fix member and its vicinity in a tissue ligating device in a modified example of the invention.

FIG. 28A is an example of a suture fix member in which a constriction part is provided in the thick direction. An end of an arm part 116 of a suture fix member 115 curves and then overlaps with one part of the arm part 116 extending from a connection part 117 in the thickness direction thereof. A gap between the overlapping arm parts 116 has an enough dimension that a suture 10 can pass through it. The overlapping arm parts form a constriction part 118. As shown in FIG. 28B, a suture 10 inserted through the constriction part 118 into a housing part 119 is unlikely to become disengaged from the housing part 119. That is, the constriction part 118 functions as a hooked suture locking part.

FIGS. 29A to 29C are examples of a suture fix member in which the housing part bends in the thick direction. FIG. 29B is a view along the arrow XXVIIb of FIG. 29A, and FIG. 29C is a view along the arrow XXVIIc of FIG. 29A. A first arm part 121A and a second arm part 121B of a suture fix member 120 curve in the thick direction of the suture fix member 120. As a result, the housing part 122 between the first arm part 121A and the second arm part 121B curves in the thick direction. With this configuration, as shown in the bottom side of FIG. 29B, a suture 10 passed through the housing part 122 easily makes contact with the side faces of the arm parts 121A and 121B forming the inner face of the housing part 122, and friction is easily generated between the side faces of the arm parts 121A and 121B and the suture 10. This prevents the suture 10 from disengaging from the housing part 122.

The hooked suture locking part formed in the thick direction in the manner described above can be combined with the configurations of the embodiments described above.

Moreover, the ligating device according to the embodiments of the invention need not include a suture needle. Even if a suture needle is not provided, the ligating device can be used for ligating a tissue without passing a suture needle through it. A conventional suture can be attached to the suture fix member just before the procedure. Therefore, a suture fix member including a hooked suture locking part can itself be distributed as a tissue ligating device.

The concepts of protrusion, constriction part, bend, and so on mentioned above are not mutually exclusive. For example, one part of an arm part forming a constriction part could be regarded as a protrusion protruding into the housing part, or vice versa. The aspect could be one where housing part curves due to the protrusion. Therefore, the hooked suture locking part is not a member that must comply with only one of the aspects described above, and can instead be formed by combining a plurality of elements.

While preferred embodiments of the invention have been described and illustrated above, it should be understood that these are exemplary of the invention and are not to be considered as limiting. Additions, omissions, substitutions, and other modified examples can be made without departing from the spirit or scope of the present invention. Accordingly, the invention is not to be considered as being limited by the foregoing description, and is only limited by the scope of the appended claims.

What is claimed is:

1. A tissue ligating device comprising:
   a suture fix member comprising:
      a connection part that defines an insertion opening through which a first part of a suture is inserted and attached;
      an engagement part comprising:
         a primary arm part extending from the connection part; and
         a first secondary arm part extending from the primary arm part,
         wherein the primary arm part and the first secondary arm part define a first housing space through which a second part of the suture is selectively inserted to be engaged by the engagement part,
wherein the primary arm part and the first secondary arm part are configured to have:
a first configuration in which a first surface point on the primary arm part is separated from a second surface point on the first secondary arm part opposing the first surface point such that the first housing space is an open space, and
a second configuration in which the first secondary arm part is deformed to bring the second surface point in contact with the first surface point such that the first housing space is a closed space, wherein the first secondary arm part is configured to be deformed to maintain the second configuration,
wherein a closed end of the first housing space is formed by a connection point between the primary arm part and the first secondary arm part, and
wherein in the first configuration, the primary arm part and the first secondary arm part are arranged such that the first housing space is an elongated space that extends along an engagement/disengagement axis away from the closed end of the first housing space toward an open end of the first housing space; and
a protrusion that opposes the connection point between the primary arm part and the first secondary arm part, wherein the protrusion intersects the engagement/disengagement axis.

2. The tissue ligating device according to claim 1, further comprising the suture.

3. The tissue ligating device according to claim 2, further comprising a suture needle attached to the suture.

4. The tissue ligating device according to claim 1,
wherein the engagement part further comprises a second secondary arm part extending from the primary arm part,
wherein the primary arm part and the second secondary arm part define a second housing space through which the second part of the suture is selectively inserted to be engaged by the engagement part, and
wherein the primary arm part and the second secondary arm part are configured to have:
a third configuration in which a third surface point on the primary arm part is separated from a fourth surface point on the second secondary arm part opposing the third surface point such that the second housing space is an open space, and
a fourth configuration in which the second secondary arm part is deformed to bring the fourth surface point in contact with the third surface point such that the second housing space is a closed space, wherein the second secondary arm part is configured to be deformed to maintain the fourth configuration.

5. The tissue ligating device according to claim 4, wherein the first secondary arm part in the first configuration and the second secondary arm part in the third configuration are formed in plane symmetry with respect to the primary arm part.

6. The tissue ligating device according to claim 1 wherein the protrusion is formed on one of the connection part, the primary arm part, and the first secondary arm part.

7. A tissue ligating device comprising:
a suture fix member comprising:
a connection part that defines an insertion opening through which a first part of a suture is inserted and attached;
an engagement part comprising:
a primary arm part extending from the connection part;
a first secondary arm part extending from the primary arm part; and
a second secondary arm part extending from the primary arm part,
wherein the primary arm part and the first secondary arm part define a first housing space through which a second part of the suture is selectively inserted to be engaged by the engagement part,
wherein the primary arm part and the first secondary arm part are configured to have:
a first configuration in which a first surface point on the primary arm part is separated from a second surface point on the first secondary arm part opposing the first surface point such that the first housing space is an open space, and
a second configuration in which the first secondary arm part is deformed to bring the second surface point in contact with the first surface point such that the first housing space is a closed space, wherein the first secondary arm part is configured to be deformed to maintain the second configuration,
wherein the primary arm part and the second secondary arm part define a second housing space through which the second part of the suture is selectively inserted to be engaged by the engagement part,
wherein the primary arm part and the second secondary arm part are configured to have:
a third configuration in which a third surface point on the primary arm part is separated from a fourth surface point on the second secondary arm part opposing the third surface point such that the second housing space is an open space, and
a fourth configuration in which the second secondary arm part is deformed to bring the fourth surface point in contact with the third surface point such that the second housing space is a closed space, wherein the second secondary arm part is configured to be deformed to maintain the fourth configuration,
wherein a closed end of the first housing space is formed by a connection point between the primary arm part and the first secondary arm part, and
wherein in the first configuration, the primary arm part and the first secondary arm part are arranged such that the first housing space is an elongated space that extends along a first engagement/disengagement axis away from the closed end of the first housing space toward an open end of the first housing space; and
a first protrusion that opposes the connection point between the primary arm part and the first secondary arm part, wherein the first protrusion intersects the first engagement/disengagement axis.

8. The tissue ligating device according to claim 7, further comprising:
the suture; and
a suture needle attached to the suture.

9. The tissue ligating device according to claim 7, wherein the first secondary arm part in the first configuration and the second secondary arm part in the third configuration are formed in plane symmetry with respect to the primary arm part.

10. The tissue ligating device according to claim 7, wherein the first protrusion is formed on one of the connection part, the primary arm part, and the first secondary arm part.

11. The tissue ligating device according to claim 7,
wherein a first surface of the primary arm part and a second surface of the first secondary arm part define the first housing space,
wherein, in the first configuration, the first surface of the primary arm part is parallel to the second surface of the first secondary arm part, and
wherein a length of the first surface along the first engagement/disengagement axis is greater than a length of the second surface along the first engagement/disengagement axis.

12. The tissue ligating device according to claim 7,
wherein a closed end of the second housing space is formed by a connection point between the primary arm part and the second secondary arm part,
wherein in the third configuration, the primary arm part and the second secondary arm part are arranged such that the second housing space is an elongated space that extends along a second engagement/disengagement axis away from the closed end of the second housing space toward an open end of the second housing space,
wherein the suture fix member further comprises a second protrusion that opposes the connection point between the primary arm part and the second secondary arm part, and wherein the second protrusion intersects the second engagement/disengagement axis.

13. A tissue ligating device comprising:
a suture; and
a suture fix member comprising:
    a connection part that defines an insertion opening through which a first part of the suture is inserted and attached;
    an engagement part comprising:
        a primary arm part extending from the connection part;
        a first secondary arm part extending from the primary arm part; and
        a second secondary arm part extending from the primary arm part,
        wherein the primary arm part and the first secondary arm part define a first housing space through which a second part of the suture is selectively inserted to be engaged by the engagement part,
        wherein the primary arm part and the first secondary arm part are configured to have:
            a first configuration in which a first surface point on the primary arm part is separated from a second surface point on the first secondary arm part opposing the first surface point such that the first housing space is an open space, and
            a second configuration in which the first secondary arm part is deformed to bring the second surface point in contact with the first surface point such that the first housing space is a closed space, wherein the first secondary arm part is configured to be deformed to maintain the second configuration,
        wherein the primary arm part and the second secondary arm part define a second housing space through which the second part of the suture is selectively inserted to be engaged by the engagement part,
        wherein the primary arm part and the second secondary arm part are configured to have:
            a third configuration in which a third surface point on the primary arm part is separated from a fourth surface point on the second secondary arm part opposing the third surface point such that the second housing space is an open space, and
            a fourth configuration in which the second secondary arm part is deformed to bring the fourth surface point in contact with the third surface point such that the second housing space is a closed space, wherein the second secondary arm part is configured to be deformed to maintain the fourth configuration,
    wherein a closed end of the first housing space is formed by a connection point between the primary arm part and the first secondary arm part, and
    wherein in the first configuration, the primary arm part and the first secondary arm part are arranged such that the first housing space is an elongated space that extends along a first engagement/disengagement axis away from the closed end of the first housing space toward an open end of the first housing space; and
    a first protrusion that opposes the connection point between the primary arm part and the first secondary arm part, wherein the first protrusion intersects the first engagement/disengagement axis.

14. The tissue ligating device according to claim 13, further comprising a suture needle attached to the suture.

15. The tissue ligating device according to claim 13, wherein the first secondary arm part in the first configuration and the second secondary arm part in the third configuration are formed in plane symmetry with respect to the primary arm part.

16. The tissue ligating device according to claim 13, wherein the first protrusion is formed on one of the connection part, the primary arm part, and the first secondary arm part.

17. The tissue ligating device according to claim 13,
wherein a closed end of the second housing space is formed by a connection point between the primary arm part and the second secondary arm part,
wherein in the third configuration, the primary arm part and the second secondary arm part are arranged such that the second housing space is an elongated space that extends along a second engagement/disengagement axis away from the closed end of the second housing space toward an open end of the second housing space,
wherein the suture fix member further comprises a second protrusion that opposes the connection point between the primary arm part and the second secondary arm part, and
wherein the second protrusion intersects the second engagement/disengagement axis.

18. The tissue ligating device according to claim 17,
wherein a first surface of the primary arm part and a surface of the first secondary arm part define the first housing space,
wherein, in the first configuration, the first surface of the primary arm part is parallel to the surface of the first secondary arm part,
wherein a length of the first surface along the first engagement/disengagement axis is greater than a length of the surface of the first secondary arm part along the first engagement/disengagement axis, wherein a second surface of the primary arm part and a surface of the second secondary arm part define the second housing space, wherein, in the third configuration, the second surface of the primary arm part is parallel to the surface of the second secondary arm part, and wherein a length of the second surface along the second engagement/disengagement axis is greater than a length of the surface of the second secondary arm part along the second engagement/disengagement axis.

* * * * *